(12) United States Patent
Levin et al.

(10) Patent No.: US 10,349,998 B2
(45) Date of Patent: Jul. 16, 2019

(54) HEAT ABLATION SYSTEMS, DEVICES AND METHODS FOR THE TREATMENT OF TISSUE

(71) Applicant: Fractyl Laboratories, Inc., Waltham, MA (US)

(72) Inventors: Phillip S. Levin, Storrs, CT (US); Jay Caplan, Belmont, MA (US); Harith Rajagopalan, Brookline, MA (US); Mark A. Manasas, Lexington, MA (US); Andrew Coats, Somerville, MA (US); J. Christopher Flaherty, Auburndale, FL (US)

(73) Assignee: Fractyl Laboratories, Inc., Lexington, MA (US)

( * ) Notice: Subject to any disclaimer, the term of this patent is extended or adjusted under 35 U.S.C. 154(b) by 588 days.

(21) Appl. No.: 14/470,503

(22) Filed: Aug. 27, 2014

(65) Prior Publication Data

US 2014/0371736 A1    Dec. 18, 2014

Related U.S. Application Data

(63) Continuation of application No. PCT/US2013/028082, filed on Feb. 27, 2013.
(Continued)

(51) Int. Cl.
*A61B 18/08*    (2006.01)
*A61B 18/04*    (2006.01)
(Continued)

(52) U.S. Cl.
CPC ............ *A61B 18/082* (2013.01); *A61B 18/04* (2013.01); *A61B 18/1492* (2013.01);
(Continued)

(58) Field of Classification Search
CPC . A61B 17/12186; A61B 18/04; A61B 18/082; A61B 18/14; A61B 18/1477;
(Continued)

(56) References Cited

U.S. PATENT DOCUMENTS 5,084,044 A    1/1992   Quint
5,190,540 A    3/1993   Lee
(Continued)

FOREIGN PATENT DOCUMENTS

CA    2666661 C    1/2015
CN    1771888 A    5/2006
(Continued)

OTHER PUBLICATIONS

Co-pending U.S. Appl. No. 14/673,565, filed Mar. 30, 2015.
(Continued)

*Primary Examiner* — Michael F Peffley
*Assistant Examiner* — Khadijeh A Vahdat
(74) *Attorney, Agent, or Firm* — Wilson Sonsini Goodrich & Rosati

(57) ABSTRACT

A system for treatment target tissue comprises an ablation device and an energy delivery unit. The ablation device comprises an elongate tube with an expandable treatment element. The system delivers a thermal dose of energy to treat the target tissue. Methods of treating target tissue are also provided.

28 Claims, 19 Drawing Sheets

Related U.S. Application Data

(60) Provisional application No. 61/603,475, filed on Feb. 27, 2012.

(51) Int. Cl.
| | |
|---|---|
| A61M 25/04 | (2006.01) |
| A61M 25/10 | (2013.01) |
| A61B 18/14 | (2006.01) |
| A61B 18/00 | (2006.01) |

(52) U.S. Cl.
CPC ......... *A61B 2018/0022* (2013.01); *A61B 2018/00023* (2013.01); *A61B 2018/0025* (2013.01); *A61B 2018/00214* (2013.01); *A61B 2018/00482* (2013.01); *A61B 2018/00494* (2013.01); *A61B 2018/00577* (2013.01); *A61B 2018/00648* (2013.01); *A61B 2018/00744* (2013.01); *A61B 2018/044* (2013.01); *A61B 2018/046* (2013.01); *A61M 25/04* (2013.01); *A61M 2025/1013* (2013.01); *F04C 2270/0421* (2013.01)

(58) Field of Classification Search
CPC ...... A61B 18/1492; A61B 2018/00023; A61B 2018/00214; A61B 2018/0022; A61B 2018/0025; A61B 2018/00482; A61B 2018/00494; A61B 2018/00577; A61B 2018/00648; A61B 2018/00744; A61B 2018/044; A61B 2018/046; A61B 2018/1472; A61B 5/4836; A61B 5/6847; A61M 25/04; A61M 25/0074; A61M 25/0084; A61M 2025/0087; A61M 2025/0089; A61M 2025/009; A61M 2025/0092; A61M 2025/1013; A61M 29/00; A61M 29/02
USPC ...................................... 606/21–41
See application file for complete search history.

(56) References Cited

U.S. PATENT DOCUMENTS

| | | |
|---|---|---|
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,871,525 A | 2/1999 | Edwards et al. |
| 5,879,347 A | 3/1999 | Saadat |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | McGuckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Edwards et al. |
| 7,530,979 B2 | 5/2009 | Ganz et al. |
| 7,556,628 B2 | 7/2009 | Utley et al. |
| 7,585,296 B2 | 9/2009 | Edwards et al. |
| 7,632,268 B2 | 12/2009 | Edwards et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,641,711 B2 | 2/2014 | Kelly et al. |
| 8,740,894 B2 | 6/2014 | Edwards |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,757,535 B2 | 9/2017 | Rajagopalan et al. |
| 2002/0013581 A1 | 1/2002 | Edwards et al. |
| 2002/0115992 A1 | 8/2002 | Utley et al. |
| 2003/0093072 A1 | 5/2003 | Friedman |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1 | 7/2004 | Callister |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |
| 2004/0220559 A1* | 11/2004 | Kramer ............... A61B 18/02 606/21 |
| 2005/0165437 A1 | 7/2005 | Takimoto |
| 2005/0171524 A1 | 8/2005 | Stern et al. |
| 2005/0203489 A1 | 9/2005 | Saadat et al. |
| 2005/0222558 A1 | 10/2005 | Baxter et al. |
| 2005/0251116 A1 | 11/2005 | Steinke et al. |
| 2005/0273090 A1 | 12/2005 | Nieman et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1* | 9/2006 | Lubock ............... A61M 25/10 600/3 |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |

(56) References Cited

U.S. PATENT DOCUMENTS

| | | |
|---|---|---|
| 2008/0147056 A1 | 6/2008 | Van Der Weide et al. |
| 2008/0207994 A1 | 8/2008 | Gonon |
| 2008/0243112 A1 | 10/2008 | De Neve |
| 2008/0275445 A1 | 11/2008 | Kelly et al. |
| 2009/0012512 A1 | 1/2009 | Utley et al. |
| 2009/0012518 A1 | 1/2009 | Utley et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0319809 A1 | 12/2011 | Smith |
| 2012/0197245 A1 | 8/2012 | Burnett et al. |
| 2012/0271277 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2015/0045825 A1 | 2/2015 | Caplan |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0081745 A1 | 3/2016 | Rajagopalan et al. |
| 2016/0310200 A1 | 10/2016 | Wang |
| 2017/0007324 A1 | 1/2017 | Kadamus et al. |
| 2017/0014596 A1 | 1/2017 | Rajagopalan et al. |
| 2018/0193078 A1 | 7/2018 | Rajagopalan et al. |
| 2018/0193590 A1 | 7/2018 | Rajagopalan et al. |
| 2018/0221622 A1 | 8/2018 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9912489 A2 | 3/1999 |
| WO | WO 02/07628 A2 | 1/2002 |
| WO | WO-02058577 A1 | 8/2002 |
| WO | WO 02/102453 A2 | 12/2002 |
| WO | WO 2003/033045 A2 | 4/2003 |
| WO | WO-03092609 A2 | 11/2003 |
| WO | WO-2006020370 A2 | 2/2006 |
| WO | WO-2007044244 A2 | 4/2007 |
| WO | WO-2008002654 A2 | 1/2008 |
| WO | WO 2010/042461 A1 | 4/2010 |
| WO | WO-2010125570 A1 | 11/2010 |
| WO | WO 2011/060301 A1 | 5/2011 |
| WO | WO-2012009486 A2 | 1/2012 |
| WO | WO 2012/099974 A2 | 7/2012 |
| WO | WO 2013/130655 A1 | 9/2013 |
| WO | WO-2013134541 A2 | 9/2013 |
| WO | WO 2013/159066 A1 | 10/2013 |
| WO | WO 2014/022436 A1 | 2/2014 |
| WO | WO 2014/026055 A1 | 2/2014 |
| WO | WO-2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2018089773 A1 | 5/2018 |

OTHER PUBLICATIONS

International search report and written opinion dated Oct. 23, 2015 for PCT/US2015/040775.
European search report and search opinion dated Aug. 4, 2015 for EP Application No. 13755156.0.
International search report and written opinion dated Jun. 26, 2015 for PCT Application No. US2015/022293.
Office action dated Aug. 5, 2015 for U.S. Appl. No. 13/945,138.
U.S. Appl. No. 14/673,565, filed Mar. 30, 2015, Rajagopalan et al.
Office action dated Mar. 12, 2015 for U.S. Appl. No. 13/945,138.
International search report and written opinion dated Dec. 24, 2014 for PCT Application No. US2014/055514.
Co-pending U.S. Appl. No. 14/917,243, filed Mar. 7, 2016
European search report and search opinion dated Mar. 8, 2016 for EP Application No. 13825257.2.
European search report and search opinion dated Mar. 17, 2016 for EP Application No. 13827149.9.
Office action dated Feb. 29, 2016 for U.S. Appl. No. 14/609,334.
Office action dated Mar. 28, 2016 for U.S. Appl. No. 14/673,565.
U.S. Appl. No. 61/603,475, filed Feb. 27, 2012, Rajagopalan et al.
U.S. Appl. No. 61/635,810, filed Apr. 19, 2012, Caplan et al.
U.S. Appl. No. 14/609,332, filed Jan. 29, 2015, Caplan et al.
U.S. Appl. No. 14/609,334, filed Jan. 29, 2015, Caplan et al.
International search report and written opinion dated Feb. 20, 2015 for PCT Application No. US2014/711601.
International search report dated Dec. 3, 2014 for PCT Application No. US2014/040957.
U.S. Appl. No. 14/515,324, filed Oct. 15, 2014, Caplan.
International search report and written opinion dated Jun. 21, 2013 for PCT/US2013/028082.
International search report and written opinion dated Jul. 13, 2012 for PCT/US2012/021739.
International search report and written opinion dated Aug. 8, 2013 for PCT/US2013/037485.
International search report and written opinion dated Nov. 8, 2013 for PCT/US2013/052786.
International search report and written opinion dated Nov. 11, 2013 for PCT/US2013/054219.
International search report and written opinion dated Dec. 30, 2013 for PCT/US2013/063753.
Miyawaki, et al. Inhibition of gastric inhibitory polypeptide signaling prevents obesity. Nat Med. Jul. 2002;8(7):738-42. Epub Jun. 17, 2002.
Rubino, et al. Potential of surgery for curing type 2 diabetes mellitus. Ann Surg. Nov. 2002;236(5):554-9.
Chathadi, et al. The role of endoscopy in amullary and duodenal adenomas. Gastrointest Endosc. Nov. 2015;82(5):773-81. doi: 10.1016/j.gie.2015.06.027. Epub Aug. 7, 2015.
Co-pending U.S. Appl. No. 15/156,585, filed Mar. 17, 2016.

(56) References Cited

OTHER PUBLICATIONS

Co-pending U.S. Appl. No. 14/956,710, filed Dec. 2, 2015.
European search report and search opinion dated Nov. 25, 2015 for EP Application No. 13777572.2.
Office action dated Nov. 30, 2015 for U.S. Appl. No. 13/945,138.
Office action dated Dec. 17, 2015 for U.S. Appl. No. 14/515,324.
U.S. Appl. No. 61/681,502, filed Aug. 9, 2012.
International Search Report and Written Opinion dated Sep. 22, 2016 for International PCT Patent Application No. PCT/US2016/040512.
Office Action dated Jan. 13, 2017 for U.S. Appl. No. 14/609,332.
Office Action dated Mar. 7, 2017 for U.S. Appl. No. 15/274,764.
Office Action dated Mar. 7, 2017 for U.S. Appl. No. 15/274,809.
Office Action dated Mar. 23, 2017 for U.S. Appl. No. 13/945,138.
Office Action dated Sep. 23, 2016 for U.S. Appl. No. 14/515,324.
Office Action dated Oct. 7, 2016 for U.S. Appl. No. 13/945,138.
Office Action dated Nov. 15, 2016 for U.S. Appl. No. 14/609,334.
Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Co-pending U.S. Appl. No. 15/406,572, filed Jan. 13, 2017.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Notice of Allowance dated Jul. 7, 2017 for U.S. Appl. No. 15/274,764.
Notice of Allowance dated Sep. 14, 2017 for U.S. Appl. No. 15/274,809.
Office Action dated May 31, 2017 for U.S. Appl. No. 15/274,764.
Office Action dated Jun. 21, 2017 for U.S. Appl. No. 14/515,324.
Office Action dated Jun. 21, 2017 for U.S. Appl. No. 14/609,334.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
"Office action dated Sep. 7, 2018 for U.S. Appl. No. 14/609,332.".
"Office action dated Oct. 4, 2018 for U.S. Appl. No. 14/515,324.".
"Office action dated Nov. 2, 2018 for U.S. Appl. No. 14/609,334".
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report with written opinion dated Feb. 1, 2018 for EP Application No. 15822378.
European search report with written opinion dated Dec. 2, 2016 for EP Application No. 14807116.
International search report with written opinion dated Jan. 9, 2018 for PCT/US2017/061074.
"Office Action dated Jul. 11, 2018 for U.S. Appl. No. 14/917,243.".
"Office Action dated Aug. 9, 2018 for U.S. Appl. No. 14/673,565.".
Office action dated Jan. 8, 2018 for U.S. Appl. No. 14/609,334.
Office action dated Apr. 4, 2018 for U.S. Appl. No. 15/156,585.
Office action dated May 18, 2018 for U.S. Appl. No. 14/956,710.
Office Action dated Nov. 2, 2017 for U.S. Appl. No. 15/156,585.
Office action dated Nov. 16, 2017 for U.S. Appl. No. 14/609,332.
Office action dated Nov. 30, 2017 for U.S. Appl. No. 14/673,565.
Office action dated Dec. 18, 2017 for U.S. Appl. No. 14/515,324.
Office action dated Dec. 19, 2017 for U.S. Appl. No. 13/945,138.
"Office action dated Mar. 7, 2019 for U.S. Appl. No. 13/945,138.".
Tolman, et al. Spectrum of liver disease in type 2 diabetes and management of patients with diabetes and liver disease. Diabetes care 30.3 (2007): 734-743.
U.S. Appl. No. 15/406,572 Office Action dated Feb. 7, 2019.

* cited by examiner

HEAT ABLATION SYSTEMS, DEVICES AND METHODS FOR THE TREATMENT OF TISSUE

CROSS-REFERENCE TO RELATED APPLICATIONS

This application is a continuation of International Patent Application No. PCT/US2013/028082, filed Feb. 27, 2013, which claims priority from U.S. Provisional Application No. 61/603,475, filed Feb. 27, 2012, the entire contents of which are incorporated herein by reference.

This application is related to PCT/US2012/021739, entitled Devices and Methods for the Treatment of Tissue, filed on Jan. 18, 2012, which claimed the benefit of U.S. Provisional Application Ser. No. 61/434,319, entitled Method and System for Treatment of Diabetes, filed Jan. 19, 2011, and of U.S. Provisional Application Ser. No. 61/538,601, entitled Devices and Methods for the Treatment of Tissue, filed Sep. 23, 2011, the contents of which are each incorporated herein by reference in their entirety.

TECHNICAL FIELD

The embodiments disclosed herein relate generally to systems, devices and methods for treating tissue, particularly gastrointestinal tissue.

BACKGROUND

Diabetes is a metabolic disease in which a person develops high blood sugar because the person's body does not produce enough insulin or the cells of the body are incapable of effectively responding to the produced insulin. Primarily, diabetes is of two types: Type-1 and Type-2. Type-1 diabetes results from to the body's failure to produce enough insulin, due to the body's autoimmune destruction of pancreatic beta cells. Type-2 diabetes, on the other hand, is a complex metabolic derangement that causes hyperglycemia through insulin resistance (in which the body's cells fail to properly utilize the produced insulin) and inadequate insulin production to meet the body's needs.

Currently, there are several procedures aimed at treating diabetes based on the above concept. The procedures require major surgery, removal of portions of the GI tract, and/or long-term implants. As with any major surgery, gastric bypass surgery carries a risk of complications.

Devices have been developed to delivery energy to the body. For example, cardiac ablation devices have been designed to delivery ablative energy to coronary tissue. Additionally, urethral resection devices have been designed to burn or cut away portions of a prostate. Each of these technologies has been modified and adapted toward effective usage in the particular portion of the body to be treated as well as the particular disease to be treated.

There is a need for systems and methods that can provide a therapeutic treatment of the GI tract by the application of energy to the GI tract. Specifically, there is a need to provide a treatment of diabetes with a procedure in the GI tract that is less invasive than gastric bypass surgery and has other advantages for patients.

SUMMARY

According to one aspect of the inventive concepts, a system for treating target tissue comprises an ablation device and an energy delivery unit. The ablation device comprises an elongate tube with a proximal portion, a distal portion, and a lumen extending from the proximal portion to the distal portion. The ablation device further comprises an expandable treatment element mounted to the elongate tube and in fluid communication with the lumen. The energy delivery unit is constructed and arranged to deliver energy to the treatment element. The system is constructed and arranged to deliver a thermal dose of energy to the target tissue.

The thermal dose may be determined prior to and/or during the treatment of the target tissue. The thermal dose may be based on one or more parameters, such as one or more parameters selected from the group consisting of: heat transfer properties of the treatment element material; heat transfer properties of the target tissue; heat transfer coefficient at the interface between the treatment element and the target tissue; and combinations thereof.

The system may comprise an algorithm wherein the thermal dose is determined by the algorithm. The algorithm may include a model of the transfer of heat into the target tissue. The algorithm may account for tissue perfusion in or proximate to the target tissue. The algorithm may be based on patient measured data, such as data gathered during the performance of a calibration routine integral to the system. The algorithm may be based on data from a large number of human and/or other mammalian subjects.

The thermal dose may comprise energy delivered by a single bolus of heated fluid that is delivered to the treatment element. The single bolus may comprise a fixed mass of heated fluid, and the single bolus may be maintained at a particular pressure or range of pressures. The single bolus pressure or pressure range may be selected to provide a function selected from the group consisting of maintaining a thermal profile; expanding the treatment element to a desired diameter; expanding the target tissue to a desired diameter; distending the target tissue; compressing a layer of the target tissue such as a mucosal layer; and combinations of these. The single bolus may comprise a single bolus mass that is based on the pressure and/or diameter of the treatment element.

The thermal dose may comprise a series of single bolus heated fluid deliveries. Alternatively or additionally, the thermal dose may comprise circulating heated fluid delivered into and out of the treatment element. The continuously delivered heated fluid may be maintained at a relatively constant temperature and/or at varied temperatures. In some embodiments, the delivered fluid is maintained at temperatures between 65° C. and 99° C. In some embodiments, fluid is delivered at a first temperature for a first time period and/or for a first volume, and fluid is delivered at a different, second temperature for a second time period and/or a second volume. The delivered, heated fluid may be a biocompatible fluid. The delivered, heated fluid may comprise a liquid, gas or gel, such as a fluid selected from the group consisting of: water; saline; perfluorinated compounds; and combinations of these.

The thermal dose may comprise a fixed duration of energy delivery. Alternatively or additionally, the thermal dose may comprise a continuously time-varying delivery of energy. The continuously time-varying delivery of energy may be provided by recirculating hot fluid through the treatment element. A heating element may be included to heat the circulating fluid, such as a heating element positioned in and/or proximate to the treatment element. The continuously time-varying delivery of energy may comprise periodic thermal dilution of fluid in the treatment element, such as when the system includes a first source of fluid and a second source of fluid, and the first source of fluid provides fluid at a temperature different than the second source of fluid.

The thermal dose may comprise a delivery of energy comprising a quasi-steady-state temperature profile. In these embodiments, the thermal dose may comprise energy delivered by a fluid maintained between 45° C. and 50° C. In these embodiments, the fluid may be recirculated in the treatment element. The system may be configured to monitor progress of target tissue ablation by monitoring time rate of energy transfer into the treatment element.

The thermal dose may comprise an energy delivered based on time-averaged temperature control over a time period.

The thermal dose may comprise energy delivered at a relatively constant temperature. In some embodiments, the thermal dose comprises energy delivered from a fluid at a temperature between 65° C. and 99° C. In some embodiments, the thermal dose comprises energy delivered from a fluid at a temperature of approximately 65° C. for a duration of approximately 30 seconds to 60 seconds. In some embodiments, the thermal dose comprises energy delivered from a fluid at a temperature of approximately 70° C. for a duration of approximately 5 seconds to 45 seconds. In some embodiments, the thermal dose comprises energy delivered from a fluid at a temperature of approximately 75° C. for a duration of approximately 3 seconds to 40 seconds. In some embodiments, the thermal dose comprises energy delivered from a fluid at a temperature of approximately 80° C. for a duration of approximately 3 seconds to 30 seconds. In some embodiments, the thermal dose comprises energy delivered from a fluid at a temperature of approximately 90° C. for a duration of approximately 3 seconds to 20 seconds.

The system may be constructed and arranged to deliver multiple thermal doses of energy to the target tissue. A first dose may be delivered to a first tissue location and a second dose delivered to a second tissue location. A first dose may be delivered at a first temperature and a second dose delivered at a temperature similar or dissimilar to the first dose temperature. In some embodiments, the second dose temperature is incrementally greater than the first dose temperature. A first dose may be applied for a first time period and the second dose may be applied for a second time period, where the first and second time periods are of similar or dissimilar lengths of time. The system may be constructed and arranged to modify one or more parameters between a first thermal dose delivery and a second thermal dose delivery, such as one or more parameters selected from the group consisting of: temperature; time duration; and combinations of these.

The system may be constructed and arranged to measure one or more ablation parameters and adjust the thermal dose based on this measurement. The measured ablation parameter may be a parameter selected from the group consisting of: temperature decay of the temperature in, on and/or near the treatment element; temperature of the target tissue; temperature of tissue proximate the target tissue; temperature of non-target tissue; temperature of fluid in the treatment element; and combinations of these. The system may be configured to stop delivery of energy based on the measurement. The system may be configured to perform a calibration procedure, such as to model temperature decay.

The system may be constructed and arranged to perform a calibration routine. The calibration routine may include the delivery of a calibration bolus. The calibration routine may comprise delivery of fluid to the treatment element, such as fluid delivered at a temperature below a level that would cause tissue ablation, such as a temperature below 41° C.

The system may comprise an algorithm based on information gathered during the calibration routine, such as an algorithm used to determine one or more thermal dose parameters. The thermal dose parameters may comprise one or more parameters selected from the group consisting of: temperature of thermal dose; temperature profile of thermal dose; duration of thermal dose; pressure applied during thermal dose; and combinations of these.

The system may be constructed and arranged to monitor residual heat present in the target tissue. The residual heat may be measured between a first delivery of energy and a second delivery of energy. The system may include a sensor, such as at least one sensor positioned on the treatment element. Signals from the at least one sensor may be used to measure residual heat.

The system may include an inflow port and an outflow port, such as an inflow port and/or an outflow port fluidly attached to one or more lumens of the ablation device. In some embodiments, the inflow port is maintained at a first pressure while the outflow port is maintained at a second pressure, less than the first pressure. In some embodiments, the inflow port is attached to a fluid delivery source (e.g. a source of fluid at a positive pressure) and the outflow port is attached to a negative pressure source.

The system may comprise a rapid thermal response time, such as a response time to inflate a treatment element and achieve a target temperature and/or a response time for a treatment element to achieve a modified target temperature. In some embodiments, the rapid thermal response time includes a thermal dose reaching 90% of a desired, modified target temperature within fifteen seconds of initiating a change to the modified target temperature. In some embodiments, the rapid thermal response time includes a rise in thermal dose temperature to 90% of a desired target temperature that occurs within five seconds of initiating the inflation of the treatment element.

The thermal dose may be constructed and arranged to ablate duodenal mucosa while avoiding damage to the duodenal muscularis propria or serosa. The thermal dose may be constructed and arranged to ablate one or more inner layers of tissue of a hollow organ while avoiding damage to one or more outer layers of a hollow organ. The thermal dose may be constructed and arranged to ablate target tissue while avoiding damage to non-target tissue.

The system may be constructed and arranged to increase the temperature of fluid in the treatment element prior to expanding the treatment element to contact the target tissue.

The treatment element may comprise a balloon. The balloon may comprise a compliant balloon or a non-compliant balloon. The treatment element may comprise multiple balloons, such as multiple individually expandable balloons and/or multiple balloons that can be individually filled with fluid.

The treatment element may comprise a balloon with multiple chambers. In some embodiments, an outer chamber at least partially surrounds an inner chamber. The inner chamber and/or the outer chamber may be filled with hot fluid configured to deliver the thermal dose. In some embodiments, the outer chamber is filled with hot fluid and the inner chamber is filled with other fluid used to radially expand the treatment element.

The treatment element may be constructed and arranged to initially expand after pressure applied internally exceeds a threshold pressure. This pressure-thresholded treatment element may be pre-heated by delivering hot fluid at a pressure below this threshold pressure, such as when the treatment element is fluidly attached to an inflow port and an outflow port of the ablation device, and the inflow port is maintained at a pressure above the outflow port pressure but below the treatment element threshold pressure. The inflow port pressure may be above room pressure while the outflow port pressure is below room pressure. The expandable treatment element may be configured such that pressurization above the threshold pressure causes the rate of heat transfer from the treatment element to target tissue to be increased, such as an increase caused by the walls of the treatment element thinning and/or the apposition between the treatment element and the target tissue increasing.

The system may be constructed and arranged to thermally prime the expandable treatment element. The thermal priming may comprise delivering heated fluid at a pressure below a pressure that would cause the treatment element to fully or partially expand. The ablation device may include an inlet port used to supply the thermal priming fluid. The ablation device may include an outlet port used to evacuate the thermal priming fluid.

The system may be constructed and arranged to rapidly inflate the expandable treatment element, such as to inflate the treatment element within ten seconds. The system may be constructed and arranged to rapidly deflate the treatment element, such as to deflate the treatment element within ten seconds.

The system may be constructed and arranged to move the target tissue away from the treatment element to stop delivery of the thermal dose to the target tissue, such as within a time period of no more than ten seconds from initiation of the target tissue movement. The tissue movement may be caused by insufflation fluid delivered by the system. Alternatively or additionally, the tissue movement may be caused by a tissue manipulator assembly of the system, such as a tissue manipulator comprising an expandable cage and/or a balloon.

The system may be constructed and arranged to move the target tissue toward the treatment element to initiate delivery of energy to the target tissue, such as within a time period of no more than ten seconds from initiation of target tissue movement. The tissue movement may be caused by removing fluid in proximity to the target tissue, such as by applying negative pressure through a lumen and/or exit port of the system, such as through the lumen or exit port of an endoscope.

The system may comprise an energy transfer modifying element constructed and arranged to improve the transfer of energy between the expandable treatment element and the target tissue. The energy transfer modifying element may comprise a coating, such as a coating selected from the group consisting of: a metal coating; a hydrogel; and combinations of these. In some embodiments, the expandable treatment element comprises a wall and the energy transfer modifying element is positioned within at least a portion of the wall. The energy transfer modifying element may comprise an element selected from the group consisting of: a wire mesh; a surface texture; one or more surface projections such as one or more projections that interdigitate with tissue; and combinations of these.

The expandable treatment element may comprise at least a portion which is permeable, such as a permeable membrane portion. The permeable portion may be constructed and arranged to deliver fluid to target tissue, such as by delivering heated, biocompatible fluid to target tissue.

The elongate tube of the ablation device may comprise multiple lumens, such as a second lumen also in fluid communication with the expandable treatment element such that fluid can be delivered into the expandable treatment element via the first lumen and extracted from the expandable treatment element via the second lumen. Pressure regulation within the first and second lumens, such as via ports connected to these lumens, can be used to aggressively inflate and/or deflate the expandable treatment element. Pressure regulation can also be used to precisely control flow through the expandable treatment element.

The system may include a second elongate tube, such as a second elongate tube of the ablation device. The second elongate tube may include a proximal portion, a distal portion and a lumen extending from the proximal portion to the distal portion. The second elongate tube may be positioned within the first elongate tube, such as to be slidingly received by the first elongate tube. Alternatively, the second elongate tube may be positioned in a side-by-side configuration with the first elongate tube. The first elongate tube and/or the second elongate tube may be configured to be advanced or retracted, such as to deliver a flow pattern delivered by the first and/or second elongate tube into the treatment element. The second elongate tube may include a port configured to extract fluid from the treatment element (e.g. fluid delivered by the first elongate tube), and the extraction port may be positioned or positionable proximal to the treatment element, such as to cause desired flow dynamics within the treatment element, such as during a thermal priming procedure or delivery of a thermal dose.

The system may comprise one or more radial support structures, such as one or more radial support structures positioned within the ablation device to prevent collapse of the elongate tube; the lumen of the ablation device; and/or the treatment element. Radial collapse may need to be prevented during high flow fluid extraction events, such as during a thermal priming procedure and/or evacuation of a thermal dose fluid from the treatment element.

The system may comprise one or more valves, such as a valve constructed and arranged to be opened to evacuate fluid from the treatment element. The valve may be positioned within the treatment element or within one or more lumens of the elongate tube, such as when a first lumen is used to fill the treatment element with fluid and a second lumen is used to evacuate fluid from the treatment element.

The system may comprise a positioning assembly constructed and arranged to position the expandable treatment element relative to tissue. The positioning assembly may include an expandable cage and a deployment shaft. A floating tube may be connected to the expandable cage and slidingly received by the ablation device such as to be retracted by retraction of the deployment shaft. The positioning assembly may comprise a radially expandable element, such as a balloon or a cage, and/or a radially extendable element such as a radially deployable arm. The positioning assembly may be constructed and arranged to position the treatment element within tubular tissue, such as to position the treatment element at the geometric center of a lumen or off-center in the lumen. The positioning assembly may be configured to position the treatment element away from tissue and/or in contact with tissue. The positioning assembly may comprise one or more deployment shafts configured to expand or extend one or more elements of the positioning assembly. The positioning assembly may be positioned proximal to the treatment element, distal to the treatment element, at the same longitudinal position as the treatment element, or combinations of these. The positioning assembly may be configured to move the treatment element away from tissue, such as a movement than occurs within five seconds or within 1 second.

The system may include an energy delivery unit, such as a syringe or other vessel containing heated fluid. The energy delivery unit may include one or more fluid heaters, such as a fluid heater positioned in a location selected from the group consisting of: within the elongate tube; within the treatment element; external to the ablation device; and combinations of these. The energy delivery unit may include a fluid pump, such as a pump that delivers and/or removes fluid to and/or from the treatment element. The energy delivery unit may provide fluid at multiple temperatures, such as a volume of fluid at a first temperature and a volume of fluid at a second temperature. The second volume of fluid may be used to change (e.g. increase or decrease) the temperature of the first volume of fluid, such as to dilute the first volume of fluid after its delivery to the treatment element.

The system may include a sensor, such as one or more sensors configured to modify an energy delivery parameter. The energy delivery parameter modified may include one or more of: energy level; power; and temperature. The sensor may include one or more sensors selected from the group consisting of: thermocouple; thermistor; resistance temperature detector (RTD); optical pyrometer; fluorometer; and combinations of these. The sensor may comprise one or more sensors constructed and arranged to measure a parameter selected from the group consisting of: pressure such as fluid pressure; flow rate; temperature such as a fluid temperature; viscosity; density; optical clarity; impedance such as tissue impedance; and combinations of these. Alternatively or additionally, the sensor may comprise one or more sensors constructed and arranged to measure a parameter selected from the group consisting of: tissue impedance such as electrical impedance and thermal impedance; tissue color; tissue clarity; tissue compliance; tissue fluorescence; and combinations of these.

In some embodiments, the sensor comprises a force sensor constructed and arranged to measure the physical contact between the expandable treatment element and the target tissue. In some embodiments, the sensor comprises a strain gauge positioned on the expandable treatment element. In some embodiments, the sensor is positioned on the ablation device such as to make contact with tissue, such as target tissue. The tissue contacting sensor may comprise a pressure and/or temperature sensor. The tissue contacting sensor may be positioned within a wall and/or on an external surface of the treatment element.

In some embodiments, the sensor comprises two or more temperature sensors, wherein at least one sensor is mounted to the expandable treatment element.

The system may comprise a controller constructed and arranged to modify delivery of the thermal dose, such as by modifying one or more of: energy delivery; temperature of a fluid delivered to the expandable treatment element; flow rate of a fluid delivered to the expandable treatment element; pressure of a fluid delivered to the expandable treatment element; and combinations of these. The controller may modify temperature, flow rate and/or pressure based on a parameter selected from the group consisting of: one or more measured properties of a delivered fluid; one or more measured properties of the expandable treatment element; one or more measured properties of the target tissue; and combinations of these.

The system may include a temperature adjusting assembly, such as an assembly comprising a first supply of fluid delivered to the expandable treatment element and a second supply of fluid delivered to the expandable treatment element. The second supply of fluid may be mixed with the first supply of fluid in the treatment element and/or at a location proximal to the first treatment element. The second supply of fluid may be configured to cool the first supply of fluid, such as a cooling performed within the treatment element.

The system may include a fluid mixing assembly constructed and arranged to cause fluid mixing within the expandable treatment element. The fluid mixing assembly may include at least one nozzle and/or at least one flow director. The fluid mixing assembly may comprise a fluid delivery tube comprising a distal delivery port and a fluid extraction tube comprising a distal extraction port. The delivery port and the extraction port may be positioned to cause fluid mixing within the expandable treatment element. The fluid delivery tube and the fluid extraction tube may be co-luminal, such as when the fluid delivery tube is positioned within the fluid extraction tube. Alternatively, the fluid delivery tube and the fluid extraction fluid may be positioned in a side-by-side arrangement.

The system may include a negative pressure priming assembly. The ablation may comprise a fluid pathway and the negative pressure priming assembly may be configured to remove fluid from this fluid pathway. The negative pressure priming assembly is constructed and arranged to improve the thermal rise time of the system.

The system may include a motion transfer element constructed and arranged to longitudinally position the expandable treatment element. In some embodiments, the target tissue comprises a first tissue portion and a second tissue portion, and the motion transfer element is configured to position the treatment element to treat the first tissue portion in a first energy delivery and to treat the second tissue portion and a subportion of the first tissue portion in a second energy delivery. The target tissue may comprise a third tissue portion and the motion transfer element may be configured to treat the third tissue portion and a subportion of the second tissue portion in a third energy delivery. The first tissue portion and the second tissue subportion may be approximately equal in length, such as when the overlap in tissue treated between treatments is approximately the same.

The target tissue treated may comprise duodenal tissue. The duodenal tissue treated may be selected from the group consisting of: at least a full length of duodenal tissue; at least a full circumference of duodenal tissue; a full mucosal layer of duodenal tissue; and combinations of these.

The system of the present inventive concepts may comprise multiple treatment elements, such as a comprising a second treatment element. In some embodiments, the ablation device includes the second treatment element. In other embodiments, the second treatment element is integral to a separate device, such as a second ablation device.

According to another aspect of the inventive concepts, a method for treating target tissue comprises providing an ablation device and delivering a thermal dose to target tissue. The ablation device comprises an expandable treatment element, and the thermal dose comprises delivering energy from the expandable treatment element to the target tissue. The thermal dose comprises one or more of: an amount of energy determined by adjusting the apposition between the treatment element and the target tissue; a thermal dose initiated by reducing the diameter of target tissue to contact the treatment element; an amount of energy delivered by a single bolus of fluid; an amount of energy delivered by a fluid maintained at a pre-determined temperature for a duration of time; an amount of energy delivered by a fluid maintained at a pre-determined temperature for a pre-determined duration of time; and a thermal dose delivered after a priming procedure has been performed.

The method may further comprise the selection of target tissue to be treated, such as multiple target tissue portion treated sequentially and/or serially. In some embodiments, a first target tissue portion receives a first thermal dose and a second target portion receives a second thermal dose.

The method may further comprise the insertion of an ablation device into a body access device. The body access device may comprise an endoscope.

The method may further comprise positioning the treatment element proximate the target tissue.

The method may further comprise performing a thermal priming procedure, such as a thermal priming procedure comprising application of negative pressure to at least a portion of the ablation device.

The method may further comprise performing a negative pressure priming procedure. The negative pressure priming procedure may remove liquid from the ablation device, such as liquid at a non-ablative temperature. The negative pressure priming procedure may remove gas bubbles from the ablation device.

The thermal dose may further comprise a continuous flow of fluid to and from the treatment element. The method may further comprise attaching a fluid inflow port of the ablation device to a fluid delivery device configured to provide this continuous flow of fluid to the treatment element. Additionally, the method may further comprise attaching a fluid outflow port of the ablation device to a negative pressure source configured to remove a continuous flow of fluid from the treatment element. The continuous flow of fluid delivered to the treatment element may comprise fluid at a relative constant temperature or fluid whose temperature changes over time.

The method may further comprise cooling the target tissue, such as cooling performed prior to, during and/or after the application of the thermal dose. The cooling may be performed with one or more cooling materials at a temperature less than 37° C. and/or less than 10° C. The cooling may be performed until at least a portion of the target tissue reaches a steady state temperature. The cooling may be performed for a first time period and the thermal dose administered for a second time period, wherein the second time period is less than the first time period.

The method may further comprise applying pressure to the target tissue and/or tissue proximate the target tissue, such as to cause a reduction of perfusion in the target tissue and/or tissue proximate the target tissue.

The method may further comprise negative pressure to a body lumen to cause target tissue to contact the treatment element, such as when the target tissue comprises tubular target tissue.

The method may further comprise confirming adequate apposition of the target tissue with the treatment element. Adequate apposition may be confirmed prior to and/or during thermal dose delivery. Confirmation may be performed using a leak test and/or a pressure measurement.

The method may further comprise performing a tissue layer expansion procedure. The tissue layer expansion procedure may comprise expansion of submucosal tissue, such as by injecting fluid into the submucosal tissue. The tissue layer expansion procedure may be performed within thirty minutes, such as within fifteen minutes of delivery of the thermal dose to the target tissue.

The method may further comprise radially expanding tubular tissue. The radial expansion may be performed by a tissue manipulating device and/or an insufflation procedure. The radial expansion may reduce one or more tissue folds.

The method may further comprise stopping delivery of the thermal dose. Stopping delivery of the thermal dose may be accomplished by one or more of: radially expanding the target tissue; radially compacting the treatment element; cooling the target tissue; and cooling the treatment element.

The method may further comprise monitoring the progress of the thermal dose delivery. The monitoring may comprise an assessment of residual heat. The monitoring may comprise an analysis of one or more signals received from one or more sensors. In some embodiments, the one or more sensors may comprise a temperature sensor. In some embodiments, the one or more sensors comprise at least one sensor selected from the group consisting of: heat sensors such as thermocouples; impedance sensors such as tissue impedance sensors; pressure sensors; blood sensors; optical sensors such as light sensors; sound sensors such as ultrasound sensors; electromagnetic sensors such as electromagnetic field sensors; and combinations of these.

The method may further comprise monitoring the impact of the thermal dose on non-target tissue.

The method may further comprise rotating and/or translating the treatment element.

The method may further comprise the delivery of a second thermal dose to target tissue. The second thermal dose may be delivered to the same target tissue and/or a second target tissue, such as second target tissue which overlaps the first target tissue. The second thermal dose may be delivered by the treatment element or a second treatment element.

According to another aspect of the invention, a method for treating target tissue comprises inserting a balloon of a treatment device into the small intestine; inflating the balloon with a heated fluid; delivering an ablative thermal dose to target tissue; measuring and controlling the temperature, pressure and/or flow rate of the delivered fluid; measuring temperature, flow rate and/or other parameters as a function of time within or between inflation cycles; applying interpretive algorithms to gathered data so as to assess treatment progress and make adjustments as needed; and maintaining the inflated balloon in contact with intestinal mucosa for a period of time sufficient to effect ablation of substantially all of the intestinal mucosa for the desired portion of intestine over the course of one or several inflation cycles.

The method may further comprise deflating the balloon to a state in which heat transfer to the mucosa has stopped. Alternatively or additionally, the method may further comprise insufflating the small intestine to a diametric configuration in which heat transfer to the mucosa has stopped.

The method may further comprise removing the balloon from the small intestine.

The method may further comprise moving the balloon to additional locations within the intestine and delivering a similar or dissimilar ablative thermal dose at each location.

The balloon may comprise a compliant balloon. The balloon may be constructed and arranged to contact a full circumferential portion of the intestinal mucosa.

The method may further comprise controlling the temperature and pressure of heated fluid in the treatment element.

The delivery of the ablative thermal dose may comprise delivering a hot fluid bolus of fixed heat content to the balloon during one or more inflation cycles.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

DETAILED DESCRIPTION OF THE DRAWINGS

Figure 1:
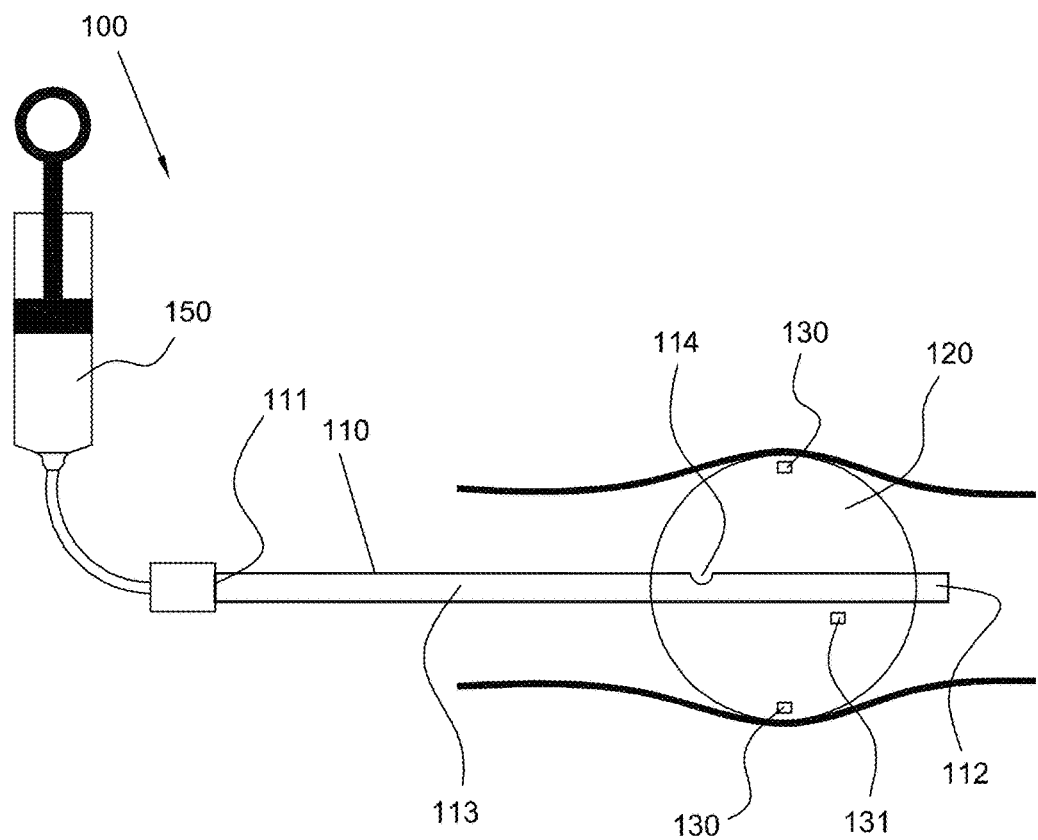
FIG. 1 is a side view of an ablation device positioned in a body lumen, the ablation device comprising an expandable balloon, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

It is an object of the present inventive concepts to provide systems, methods and device for safely and effectively ablating a volume of tissue (the "target tissue"), such as one or more layers of a portion of tubular or solid tissue, such as tissue of an organ or tissue of the gastrointestinal tract of a patient. The systems and device of the present inventive concepts include one or more treatment elements to treat the target tissue, such as expandable treatment elements configured to be expanded to contact the target tissue and/or treatment elements configured to be positioned at a location to which target tissue is manipulated toward. A treatment element may be configured to treat target tissue in one or more locations of the patient, such as one or more contiguous or discontiguous locations. The target tissue comprises a three dimensional volume of tissue, and may include a first portion, a treatment portion, whose treatment has a therapeutic benefit to a patient; as well as a second portion, a safety margin portion, whose treatment has minimal or no adverse effects to the patient. Non-target tissue may be identified comprising tissue whose treatment by the treatment element is reduced or avoided.

The target tissue treatment may include one or more effects to the target tissue such as an effect selected from the group consisting of: modification of cellular function; cell death; apoptosis; instant cell death; cell necrosis; denaturing of cells; removal of cells; and combinations of these. Target tissue may be selected such that after treatment the treated target tissue and/or tissue that replaces the target tissue functions differently than the pre-treated target tissue. The modified and/or replacement tissue may have different secretions or quantities of secretions than the pre-treated target tissue, such as to treat diabetes or obesity. The modified and/or replacement tissue may have different absorptive properties than the target tissue, such as to treat diabetes; obesity and/or hypercholesterolemia. The effect of the treatment may occur acutely, such as within twenty four hours, or after longer periods of time such as greater than twenty four hours or greater than one week.

Target tissue to be treated may comprise two or more tissue portions, such as a first tissue portion treated with a first treatment and/or a first treatment element, and a second tissue portion treated with a second treatment and/or second treatment element. The first and second tissue portions may be adjacent and they may contain overlapping volumes of tissue. The first and second treatment and/or treatment elements may be similar or dissimilar. Dissimilarities may include type and/or amount of energy to be delivered by an energy delivery treatment element. Other dissimilarities may include but are not limited to: target tissue area treated; target tissue volume treated; target tissue length treated; target tissue depth treated; target tissue circumferential portion treated; energy delivery type; energy delivery rate and/or amount; peak energy delivered; average temperature of target tissue treatment; temperature profile of target tissue treatment; duration of target tissue treatment; and combinations of these.

Target tissue may include tissue of the duodenum, such as tissue including all or a portion of the mucosal layer of the duodenum, such as to treat diabetes or obesity while leaving the duodenum anatomically connected after treatment. Replacement tissue may comprise cells that have migrated from one or more of gastric mucosa; jejunal mucosa; and/or an untreated portion of the duodenum whose mucosal tissue functions differently than the treated mucosal tissue functions prior to treatment. In some embodiments, target tissue includes treatment tissue comprising the mucosal layer of the duodenum, and safety margin tissue comprising a full or partial layer of the submucosal layer of the duodenum. In some embodiments, the target tissue comprises the entire length of the mucosal layer of the duodenum, and may include a portion of the pylorus contiguous with the duodenal mucosa and/or a portion of the jejunum contiguous with the duodenal mucosa. Treatment of duodenal tissue may be performed to treat a disease or disorder selected from the group consisting of: diabetes; obesity; insulin resistance; a metabolic disorder and/or disease; and combinations of these. A full circumferential portion (e.g. 360°) of the mucosal layer is typically treated.

Target tissue may comprise tissue of the terminal ileum, such as to treat hypercholesterolemia or diabetes. In this embodiment, the target tissue may extend into the proximal ileum and/or the colon.

Target tissue may comprise gastric mucosal tissue, such as tissue regions that produce ghrelin and/or other appetite regulating hormones, such as to treat obesity or an appetite disorder.

Target tissue may comprise bladder wall tissue, such as to treat a disease or disorder selected from the group consisting of: interstitial cystitis; bladder cancer; bladder polyps; pre-cancerous lesions of the bladder; and combinations of these.

Target tissue may comprise tissue selected from the group consisting of: large and/or flat colonic polyps; margin tissue remaining after a polypectomy; and combinations of these. These tissue locations may be treated to treat residual cancer cells.

Target tissue may comprise airway lining tissue, such as to treat a disease or disorder selected from the group consisting of: bronchoalveolar carcinoma; other lung cancers; pre-cancerous lung lesions; and combinations of these.

Target tissue may comprise at least a portion of the intestinal tract afflicted with inflammatory bowel disease, such that Crohn's disease or ulcerative colitis may be treated.

Target tissue may comprise tissue of the oral cavity, such as to treat one or more of: oral cancers and a pre-cancerous lesion of the oral cavity.

Target tissue may comprise tissue of the nasopharynx, such as to treat nasal polyps.

Target tissue may comprise gastrointestinal tissue selected to treat Celiac disease and/or to improve intestinal barrier function.

The treatment elements, systems, devices and methods of the inventive concepts may be constructed and arranged to reduce or avoid treating certain tissue, termed "non-target tissue" herein. Depending on the location of treatment, different non-target tissue may be applicable. In certain embodiments, non-target tissue may comprise tissue selected from the group consisting of: the tunica serosa, the tunica muscularis and/or the outermost partial layer of the submucosa such as during mucosal treatment; Ampulla of Vater such as during mucosal treatment proximate the Ampulla of Vater; pancreas; bile duct; pylorus; and combinations of these.

It is another object of the present inventive concepts to provide a device for delivering a suitable thermal dose, "thermal dose" defined herein to be the combined effect on the target tissue of thermal application time and thermal application temperature. This thermal dose is typically selected to effect ablation of the target tissue by transferring thermal energy from a heated fluid contained within a balloon. In an alternative embodiment, a chilled fluid may be used to cryoablate the target tissue, similarly with a thermal application time and a thermal application temperature. The term "fluid" as used herein shall be understood to refer to any flowable material, including liquids, gases and gels, such as one or more materials configured to be delivered to a treatment element such as a balloon, and to deliver a thermal dose to target tissue. The thermal dose may be of a pre-determined magnitude and/or it may be selected and/or modified during treatment. During the treatment, target tissue ablation may be monitored and/or adjusted. A dynamic endpoint for treatment may be determined through ablation monitoring, such as an endpoint determined by one or more factors measured during delivery of the thermal dose or during a non-treatment dose such as a calibrating dose. The device may be part of a system which includes a controller, such as for providing hot fluid to the balloon and for monitoring and controlling temperature and/or pressure of the balloon fluid.

The present inventive concepts provide a method for ablating the mucosa of a portion of the small intestine, comprising the steps of: inserting a balloon of a treatment device into the small intestine, such as a compliant balloon; inflating the balloon with a heated fluid so that the balloon is in contact with substantially all of the mucosa for which necrosis or other treatment is desired; delivering an ablative thermal dose to the target tissue such as by controlling the temperature and pressure of the fluid during the treatment time or by delivering a hot fluid bolus of fixed heat content to the balloon during one or several inflation cycles; measuring and controlling the temperature, pressure and/or flow rate of the delivered fluid by associated measuring and/or controlling means, including but not limited to, sensors, heaters, pumps, valves, and ballasts where the measuring and/or controlling means may be external to the patient's body or may reside in part or completely within the treatment device itself; measuring temperature, flow rate and/or other parameters as a function of time within or between inflation cycles and applying interpretive algorithms to the gathered data so as to assess treatment progress and make adjustments as needed; maintaining the inflated balloon in contact with the mucosa for a period of time sufficient to effect ablation of substantially all of the mucosa for the desired portion of intestine over the course of one or several inflation cycles; deflating the balloon to a state in which heat transfer to the mucosa is stopped; and removing the balloon from the small intestine or moving the balloon to additional locations within the intestine such that the foregoing treatment cycle may be repeated until all of the target tissue has been treated. Treatment of additional locations may comprise treating contiguous and/or overlapping tissue segments. Treatment of a second location may be performed after a time period which is initiated after completion of treatment of a first location, such as after a time period configured to allow one or more portions of tissue to cool, such as to cool to body temperature.

The inventive concepts relate to the conductive transfer of heat from a hot fluid, which is contained within an inflatable balloon, to the inner surface of a body organ. Additionally or alternatively, cryoablation by fluids at low temperatures can be performed. Living tissue may be selectively ablated by the application of heat through a combination of time and temperature. Elevated temperature ablation of living tissue exhibits a temperature threshold, below which the application of heat over any time duration, short or long, is non-destructive of tissue and above which the application of heat is increasingly damaging with increasing time and/or temperature, to the point of necrosis. This elevated temperature threshold, as well as the amount of tissue damage that results over time during application of heat above this threshold, may be different for different cells or organ types and may derive in part from the natural perfusion of blood through living tissues and the consequent dissipation of applied heat by the flowing blood. Systems, methods and devices of the present inventive concepts may be configured to treat a first tissue type and/or a first tissue location with a different thermal dose than the thermal dose used to treat a second tissue type and/or second tissue location, respectively, such as due to the local perfusion or other local tissue parameter.

In the embodiments described in reference to the figures herebelow, rapid and efficient heat transfer from a balloon to target tissue is achieved via a heat transfer fluid, either delivered as a hot fluid bolus (e.g. the administration of one or more individual, treatment element-filling volumes of hot fluid), or continuously delivered as re-circulating hot fluid. Suitable fluids include high heat capacity fluids, such as biocompatible fluids such as water or saline, as well as fluids with high thermal conductivity, such as perfluorinated compounds.

As described herein, room pressure shall mean pressure of the environment surrounding the systems and devices of the present inventive concepts, sometimes referred to as gauge pressure. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure may include a vacuum but does not imply a pressure below a vacuum.

The balloons of the present inventive concepts may be divided into two general categories: those that are composed of a substantially elastic material, such as silicone, latex, low-durometer polyurethane, and the like; and those that are composed or a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness may be combined to produce a balloon that exhibits a measurable pressure-threshold for inflation, i.e. the balloon becomes inflated only after a minimum fluidic pressure is applied to the interior of the balloon; and a second sub-category, wherein the balloon expands elastically until an elastic limit is reached which effectively restricts the balloon diameter to a maximum value. It will be understood that the individual properties of the balloons in each of these categories may be applied to one or more advantages in the specific embodiments disclosed herein, these properties integrated singly or in combination. By way of example only, one or more of the following configurations may be employed: a highly elastic balloon may be used to achieve a wide range of operating diameters during treatment, e.g. during operation a desired balloon diameter may be achieved by adjustment of a combination of fluid temperature and pressure; a substantially inelastic balloon or a balloon that reaches its elastic limit within a diameter approximating a target tissue diameter (e.g. a duodenal mucosal diameter) may be used to achieve a relatively constant operating diameter that will be substantially independent of operating pressure and temperature; a balloon with a pressure-threshold for inflation may be used to maintain an uninflated diameter during relatively low pressure conditions of fluid flow and then achieve a larger operating diameter at higher pressure conditions of flow. Pressure-thresholded balloons may be configured in numerous ways. In one embodiment, a balloon is configured to have a relatively thick wall in its uninflated state, such as to minimize heat transfer out of the balloon and into the surrounding tissue while the balloon is maintained in this uninflated state. The balloon may be further configured such that its wall thickness decreases during radial expansion (e.g. as is described in reference to FIGS. 6A-6D herebelow). In another embodiment, a balloon is configured to have a relatively small diameter in its uninflated state (e.g. a diameter small relative to the inner diameter of tubular target tissue such as the diameter of the mucosal layer of duodenal wall tissue), such as to minimize or completely eliminate apposition between the balloon and the surrounding tissue to minimize heat transfer into the surrounding tissue until the balloon is fully inflated. In another embodiment, a balloon and device are configured to circulate a flow of hot fluid through the balloon (e.g. an elastic balloon or an inelastic balloon) at a sufficiently low enough pressure to prevent apposition of the balloon with target tissue, such as to pre-heat one or more surfaces of the ablation system and/or ablation device that are in fluid communication with the balloon. In this configuration, when the balloon is fully inflated, the temperature of the fluid of the balloon will be at a desired level or it will rapidly and efficiently reach the desired level for treatment (i.e. minimal heat loss to the fluid path components due to the pre-heating). These configurations provide a method of "thermal priming" prior to target tissue treatment, whereby the balloon and its fluid delivery system are placed in a state of maximum readiness for the administration of heat to the target tissue, such as to avoid delays due to undesired cooling from one or more fluids or device components at a lower temperature than the hot fluid delivered to the balloon for treatment. Alternatively, a similar procedure may be performed with a chilled fluid, such as when the balloon is configured to cryoablate tissue. Each of these configurations is useful singly and in combination for those cases where the treatment temperature in the balloon must be established very rapidly upon inflation. For example, a balloon with a pressure threshold for inflation may also, upon inflation, reach its elastic limit within a diametric range applicable to the target tissue being treated. In some embodiments, priming such as thermal priming may include a purge with a gas (e.g. air) prior to the delivery of the priming fluid. In some embodiments, priming such as thermal priming may include an evacuation procedure prior to the delivery of the priming fluid. Presence of gas bubbles may lead to undesired non-uniform or otherwise inaccurate transfer of heat energy to the target tissue. A fluid evacuation step may comprise application of a vacuum or other negative pressure source to one or more fluid pathways to subsequently be primed or otherwise filled, such as to eliminate or otherwise reduce gas bubbles. The advantages of these embodiments as they relate to various treatment conditions and modalities are described immediately herebelow in reference to a first treatment modality and a second treatment modality, and will be further elaborated in reference to the figures described herein.

Treatment Modality 1: APPOSITION BETWEEN THE BALLOON AND THE TARGET TISSUE IS ESTABLISHED BY ADJUSTING THE BALLOON DIAMETER. At those times during treatment when it is desirable to increase or otherwise modify heat transfer between the balloon and the target tissue, the balloon diameter may be increased in situ so as to conform to the native diameter of the target tissue, such as to the native diameter of tubular tissue such as duodenal wall tissue. At those times during treatment when it is desirable to decrease heat transfer between the balloon and the target tissue, the balloon diameter may be reduced in situ, such as to prevent or reduce contact of the balloon with the target tissue. For those cases where the native diameter of the tissue varies substantially within the treatment zone, then a highly elastic or compliant balloon may be employed, such as a balloon which may be adjusted to achieve a wide range of operating diameters. For those cases, where a short-duration thermal treatment is desired, as for example, a thermal dose application of less than 30 second duration, then a pressure-threshold balloon may be used, such as when thermal priming is employed prior to inflation.

Treatment Modality 2: APPOSITION BETWEEN THE BALLOON AND THE TARGET TISSUE IS ESTABLISHED BY CONTROLLING THE DIAMETER OF THE TARGET TISSUE. To initiate and/or increase heat transfer between a treatment element, such as a balloon, and the target tissue, the diameter of the target tissue may be decreased in situ so as to approximate and/or conform to the diameter of the balloon. To decrease heat transfer between the treatment element, such as a balloon, and the target tissue, the diameter of the target tissue may be increased in situ, so as to prevent or reduce contact of tissue (e.g. target tissue or non-target tissue) with a treatment element. The diameter of the tissue proximate a treatment element may be increased or decreased, independently of the treatment element diameter, by means of a variety of fluids that may be administered within and/or withdrawn from the target-tissue lumen, such as using insufflation techniques knows to those of skill in the art. Typical insufflation fluids include but are not limited to: gases such as $CO_2$ or air; liquids such as saline solution; and combinations of these. The insufflation fluids may be introduced through the ablation device, through an endoscope such as an endoscope through which the ablation device is inserted, or via another device placed proximate the target tissue. Delivery of insufflation fluids may be performed to manipulate tissue such as to distend tissue. Alternatively or additionally, delivery of insufflation fluids may be performed to move target tissue away from a treatment element, such as to stop transfer of energy to target tissue at the end of a thermal dose period. Removal of these insufflation fluids and/or the application of a vacuum or other negative pressure by one or more of the devices described immediately hereabove, can be used to decrease the diameter of the target tissue, such as to bring the target tissue in contact with a treatment element. In this tissue diameter controlled approach, a balloon that may be maintained at a substantially constant diameter may be desirable, such as a substantially inelastic balloon such a balloon with an elastic-limit. When a short-duration thermal treatment is desired, as for example, a thermal application of less than 30 second duration, then a pressure-thresholded balloon may also be desirable.

Referring now to FIG. 1, a tissue treatment device with its treatment element positioned in a body lumen is illustrated, in accordance with the present inventive concepts. Device 100 includes shaft 110 having proximal end 111 and distal end 112. Device 100 also includes balloon 120, positioned on a distal portion of shaft 110 and configured to be inflated by introducing fluid into a lumen 113 which exits shaft 110 through opening 114, such that balloon 120 expands to contact target tissue, such as the luminal wall tissue shown in contact with balloon 120. Opening 114 may comprise multiple openings, not shown. Opening 114 may be positioned in one or more locations, such as to adjust the flow dynamics of fluid delivered into and/or removed from balloon 120. Inflation of balloon 120 with hot fluid delivers thermal energy to the target tissue through the wall of balloon 120. Balloon 120, and the other balloons of the inventive concepts provided herein, may comprise a compliant balloon; a non-compliant balloon; a balloon with a pressure threshold; a balloon with compliant and non-compliant portions; and combinations of these. In the illustrated embodiment, the thermal dose required to limit ablation to a thin inner layer of a target tissue is achieved by means of a heated fluid "bolus" (i.e. a fixed mass of hot fluid) that is injected into an empty or deflated balloon, for example, balloon 120 (shown in an inflated state in FIG. 1). As shown, the precise mass of fluid that is injected into balloon 120 may be controlled by controlling the volume delivered (as by a syringe 150 positioned at proximal end 111 and in fluid communication with lumen 113). In an alternative embodiment, the precise mass of fluid that is injected into balloon 120 can be controlled through pressure control or measurement, such as by pressure regulation during balloon inflation. In some embodiments, balloon 120 is an inelastic balloon or otherwise reaches an elastic limit, and the mass of fluid is achieved (i.e. controlled) when balloon 120 is completely filled, for example when a complete fill is confirmed when a rapid rise in balloon pressure occurs (e.g. as detected by one or more pressure sensors, not shown but in fluid communication with balloon 120 and/or in contact with balloon 120). In some embodiments, balloon 120 is an elastic balloon and the mass of fluid is achieved based on a predetermined delivery volume and/or when the pressure in balloon 120 reaches a pre-determined pressure or balloon 120 reaches a pre-determined amount of stretch (e.g. as measured by a strain gauge mounted in or on balloon 120). As an elastic balloon 120 is filled with fluid, pressure will increase continuously, typically at an expected rate, until apposition with tissue is initiated. Additional fluid delivered causes the pressure to change at an increased rate (i.e. higher change of pressure per unit volume of fluid delivered after initial apposition). Pressure measured at the inflexion point (i.e. the change in rate of pressure increase), hereinafter "apposition pressure", represents the pressure necessary to achieve initial apposition of balloon 120 with tissue at that particular target tissue location. In some embodiments, amount of fluid delivered to balloon 120 comprises a volume of fluid whose delivery causes balloon 120 to be pressurized at the apposition pressure. In other embodiments, additional fluid is delivered to cause balloon 120 to be pressurized to a level above apposition pressure, such as a predetermined amount of additional fluid or an amount of additional fluid delivered to achieve a predetermined increase in pressure above apposition pressure. Device 100 may be configured to regulate pressure within balloon 120 to provide a function selected from the group consisting of: maintaining a thermal profile; expanding balloon 120 to a desired diameter; expanding the target tissue to a desired diameter; distending the target tissue; compressing a layer of the target tissue such as a mucosal layer; and combinations of these. When the mass of the thermal dose bolus is fixed, the values of temperature and heat capacity of the fluid determine the total heat content of the injected bolus and thereby determine the maximum deliverable thermal dose for a given inflation cycle of balloon 120.

For a given starting temperature of the bolus, the time duration of the heat application may be less critical or less specifically controlled since the total treatment energy delivered is based primarily on this starting bolus temperature. A complete cycle of this particular embodiment is understood to comprise the rapid inflation of the balloon with a heated bolus of fluid, the temperature decay of the bolus to either a sub-threshold level or to any pre-determined temperature level as it transfers heat to the target tissue, and the subsequent emptying of balloon 120 (e.g., by an applied vacuum or other negative pressure applied to lumen 113). In some embodiments, one or several repeat hot fluid fill and emptying cycles may be applied to the target tissue to effect complete treatment at any given location. Each cycle may comprise a similar or dissimilar starting bolus temperature.

By consideration of the heat transfer properties of the hot fluid in the balloon and the balloon material, as well as the heat transfer properties of the target tissue (including the composition of the tissue and the rate of blood perfusion within the tissue), along with the heat transfer properties at the interface between balloon 120 and the target tissue, the correct temperature of the bolus may be selected to effectively ablate the target tissue. Collectively, these various heat transfer properties are manifested in a single measurable variable: the temperature decay rate of the bolus, which may be monitored by one or more temperature sensors 130 that are positioned on, within the wall of, and/or within the cavity of balloon 120. Signals received from the one or more temperature sensors 130 are interpreted through one or more treatment algorithms, as are described herebelow. Temperature sensors 130 may be positioned to measure the temperature of target tissue, tissue proximate target tissue, and/or non-target tissue. One or more algorithms of device 100 may use the signals provided by the one or more sensors 130 to adjust the thermal dose, such as to adjust the temperature of one or more fluids delivered to and/or circulating within balloon 120, and/or to cause balloon 120 to rapidly deflate, ceasing delivery of thermal energy from balloon 120 to the target tissue. Ceasing of energy delivery may also be caused by radial expansion of tubular target tissue, such as via an insufflation of gastrointestinal or other luminal wall tissue as is described hereabove. Device 100 may include control means, such as those described in reference to FIG. 19 herebelow, such that one or more algorithms can control fluid delivery based on signals from the one or more sensors 130. An algorithm may account for the distance between the sensor and the treatment element and/or the distance between the sensor and the target tissue.

The state of necrosis of the target tissue and the health of any underlying, non-target tissue may be monitored by monitoring the rate of temperature decay of the applied bolus. The rate of temperature decay is related to the perfusion rate of blood through the target tissue and through the underlying tissue. Therefore, the necrosis of the target tissue and the associated shut-down of perfusion within that tissue is expected to be accompanied by a reduction in the rate of heat transfer. Simultaneously, the continuing perfusion and therefore the continuing viability of the non-targeted underlying tissue will be indicated by a minimum rate of temperature decay. The rate and shape of the temperature decay curve of the bolus carries useful information, such as information used to monitor the progress of the ablation and/or to optimize the target tissue treatment. The temperature decay curve may be monitored precisely by means of one or more temperature sensors 130. Such sensors 130 typically include one or more sensors selected from the group consisting of: thermocouple; thermistor; resistance temperature detector (RTD); optical pyrometer; fluorometer; and combinations of these. Additionally or alternatively, device 100 may include one or more other sensors 131, such as one or more other sensors constructed and arranged to measure: pressure such as fluid pressure; flow rate; temperature sensor such as a fluid temperature sensor; viscosity; density; optical clarity; and combinations thereof. Alternatively or additionally, sensors 131 may comprise one or more sensors constructed and arranged to measure a parameter selected from the group consisting of: tissue impedance such as electrical impedance and thermal impedance; tissue color; tissue clarity; tissue compliance; tissue fluorescence; and combinations thereof. In one embodiment, sensor 131 comprises a force sensor constructed and arranged to measure the physical contact between the expandable treatment element and the target tissue. In another embodiment, sensor 131 comprises a strain gauge positioned on the expandable treatment element. In another embodiment, sensor 131 is positioned on device 100, such as a sensor selected from the group consisting of: a sensor positioned to contact target tissue or other tissue; a pressure sensor; a temperature sensor; a sensor attached to an external portion of balloon 120; a sensor positioned within a wall of balloon 120; and combinations of these.

In one embodiment, optimization of a treatment cycle may be achieved by adjusting temperature and duration in one or more cycles and/or by terminating one or more cycles, such as an adjustment or termination based upon observed changes in the shape of the temperature decay curve. In some embodiments, ablation may be approached in incremental steps, such as by applying a first "calibration bolus" to the target tissue, for example, a calibration cycle including the application of a sub-threshold temperature bolus (e.g. via fluid delivered to balloon 120 at 41° C.) for which the natural decay rate of target tissue would be recorded. A subsequent treatment cycle or cycles would then be incrementally increased in temperature such that the evolving shape of the decay curve could be quantitatively monitored based on information recorded during the calibration cycle, such as to determine the onset and progress of ablation. An algorithm may include a mathematical model of the heat transfer into the target tissue based on information collected in the calibration cycle. The algorithm may be defined or refined by empirical correlation, such as via information collected in a second calibration cycle and/or information collected during one or more treatment steps.

In some embodiments, the effect of increased blood perfusion due to the application of heat to soft tissue can be included in the analysis of the temperature decay curve, such as when this effect is found to be a significant factor when delivering heat energy to the target tissue. The magnitude of this effect may be determined in a calibration cycle, such as the calibration cycle described hereabove. Alternatively, the target tissue may be characterized using data from a general patient population, such as data collected prior to the initiation of a treatment cycle. Additionally or alternatively, data from the specific patient may be used to characterize the target tissue, such as data collected in a calibration cycle, data collected in a treatment cycle, and/or other data.

Figure 19:
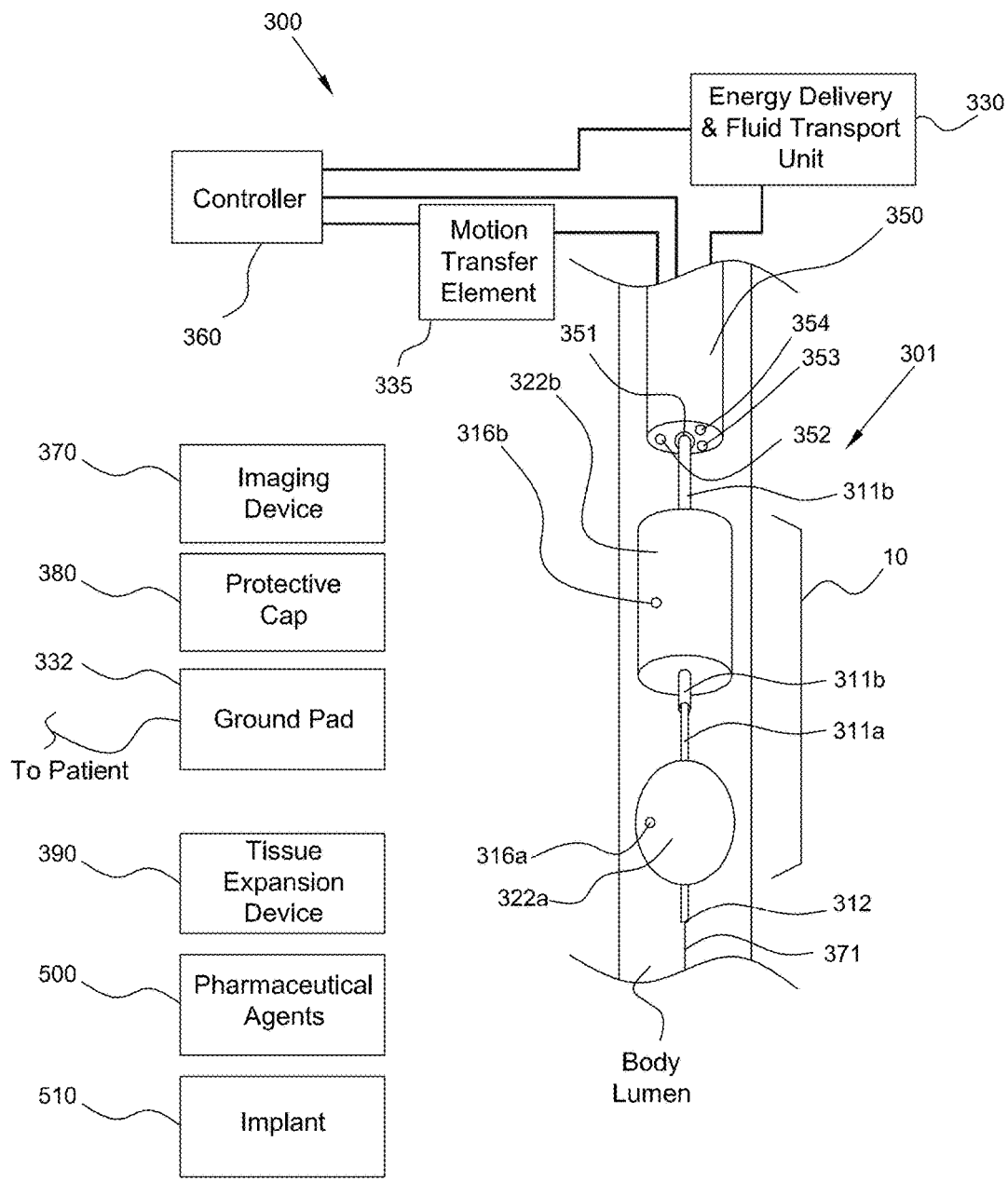
FIG. 19 is a schematic view of a system for treating tissue, consistent with the present inventive concepts.

Device 100 may be part of an ablation system, such as an ablation system including a temperature controlled fluid delivery device as is described in reference to FIG. 19 herebelow. Balloon 120, and the other treatment elements of the present inventive concepts, may be configured to be rotated, translated, moved in a helical spiral, or otherwise repositioned prior to a tissue treatment, during a tissue treatment, after a tissue treatment and/or between treatment of a first portion of tissue and a second portion of tissue. Movement of balloon 120 may be manual and/or automated, such as via automation provided by one or more motion transfer mechanisms described in reference to ablation system 300 of FIG. 19 herebelow.

Figure 2:
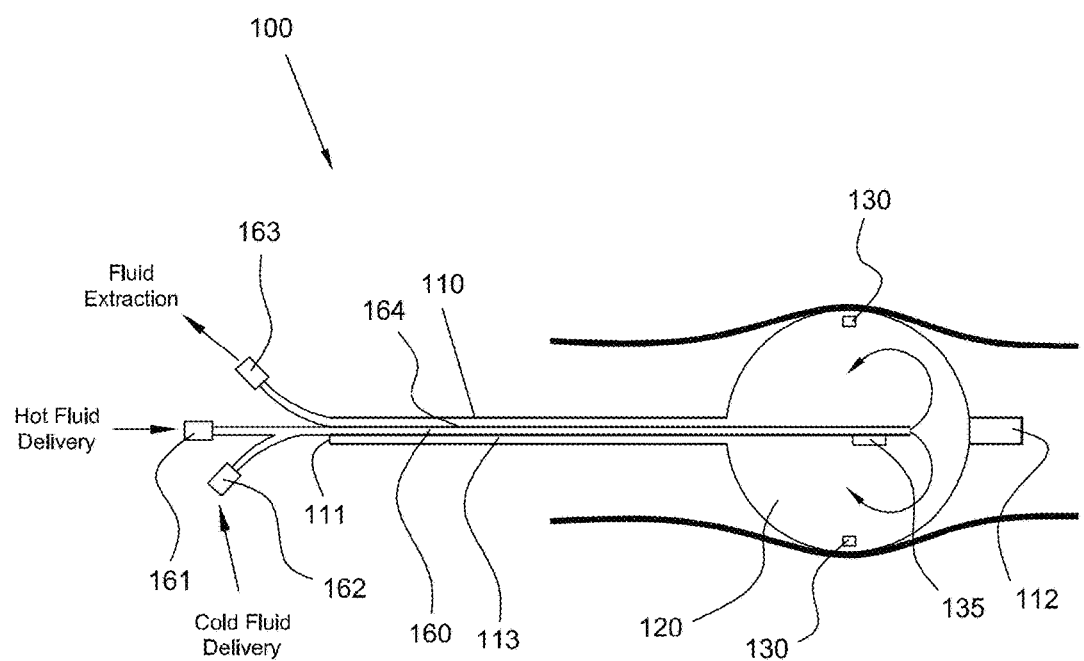
FIG. 2 is a side view of an ablation device positioned in a body lumen, the ablation device comprising an inner shaft, an outer shaft and an expandable balloon, consistent with the present inventive concepts.

FIG. 2 illustrates a device for treating tissue, positioned in a body lumen and including an inner shaft, an outer shaft, and an expandable balloon, in accordance with the present inventive concepts. Device 100 includes a proximal end 111, a distal tip 112 and a shaft 110. Shaft 110 includes a lumen 113 therethrough. Lumen 113 is in fluid communication with port 163. Positioned within shaft 110 is shaft 164, which surrounds lumen 160. Shaft 164 includes port 161 and port 162, each in fluid communication with lumen 160. In one embodiment, hot fluid is delivered to port 161 and fluid having a lower temperature than the hot fluid enters port 162. Fluid delivered through port 162 can be used to increase or decrease the temperature of the fluid in balloon 120. Fluid delivered through port 162 can be used to modulate the temperature of the fluid in balloon 120. Port 163 is configured to be attached to a pumping or negative pressure source configured to create an outflow of fluid from lumen 113. Device 100 also includes balloon 120 configured to be inflated such that balloon 120 contacts target tissue and enables treatment of the target tissue through the wall of balloon 120. In the illustrated embodiment, the control of the surface temperature of balloon 120 may be achieved by continuous circulation of hot fluid into and out of balloon 120 via lumen 160 of shaft 164, which is circumferentially surrounded by lumen 113. Fluid flowing through lumen 113 may be configured as an insulator, reducing undesired cooling of fluid flowing through lumen 160 by the cooler environment surrounding shaft 110.

The distal end of lumen 160 is typically positioned in a distal portion of balloon 120, as shown in FIG. 2. The distal end of lumen 113 is typically positioned in a proximal portion of balloon 120, also as shown. Staggered positioning of the exit ports of lumens 160 and 113 causes mixing of fluid introduced into balloon 120. While the distal end of lumen 113 is shown positioned at the proximal end of balloon 120, shaft 110 may extend to a more distal portion of the internal volume of balloon 120, such as to change the flow dynamics within balloon 120. Similarly, the distal end of lumen 160 may be positioned in numerous locations within balloon 120, such as to modify the flow dynamics within balloon 120. One or more flow directors may also be included to cause fluid mixing, such as those described in reference to FIG. 15 herebelow. In some embodiments shaft 164 is slidingly received by shaft 110, such that the distal end of shaft 164 and lumen 160 can be advanced and retracted, such as to modify the flow dynamics within balloon 120. Alternatively or additionally, shaft 110 may be configured to be advanced and/or retracted, such as to reposition the distal end of lumen 160. While lumens 113 and 160 are shown in a concentric geometry, these and other lumens of the present inventive concepts may be positioned in numerous configurations including but not limited to: concentric; side-by-side; eccentric (e.g. off-center); helical; and combinations of these. Device 100 may include a heating element, such as heating element 135 positioned within balloon 120. Alternatively or additionally, one or more heating elements can be positioned in or proximate to a fluid pathway, such as one or more fluid pathways present in lumens 113 and/or 160, or one or more fluid pathways in fluid communication with lumens 113 and/or 160. A control loop may be established wherein balloon 120 surface temperature, as measured with one or more temperature sensors 130, serves as a feedback parameter, and the time rate of energy transfer into balloon 120 serves as the control variable. The time rate of energy transfer into balloon 120 can be measured, such as by measuring the temperature and/or flow rate of the fluid, the power transfer into heating element 135, and/or by another measurement, such as to monitor the progress of the ablation. As discussed in reference to FIG. 1, indications of the onset and progress of ablation are expected to be manifested by changes in the rate of energy transfer that are required to maintain a constant or predetermined temperature at the surface of balloon 120. The onset of ablation may be gradually approached from treatment cycle to treatment cycle by incrementally increasing the temperature level of the treatment element. The integrated time rate of energy transfer may provide a means of monitoring the total accumulated thermal dose.

In one embodiment, the thermal dose required to limit ablation to a relatively thin, inner layer of target tissue is achieved by means of a continuously time-varying application of heat. The desired time variation may be accomplished, for example, by means of a re-circulating hot-fluid that passes over a modulated heater, such as heater 135, typically a resistive or other heater connected to one or more wires, not shown but traveling proximally and electrically attached to a supply of power. Alternatively, the desired time variation may be accomplished by a process of periodic thermal dilution of a re-circulating hot fluid. Thermal dilution is herein defined as the rapid lowering of the temperature of a circulating heat transfer fluid by means of the introduction of a second fluid of lower temperature. For example, a hot fluid can be delivered and/or re-circulated via port 161, and thermal dilution can be achieved by introducing a fluid of lower temperature via port 162. In one embodiment, a first fluid at a temperature at or above 65° C., such as a temperature between 65° C. and 99° C., will be delivered to balloon 120 for at least 3-5 seconds, followed by the introduction of a second fluid at a temperature below 43° C. for at least 3-5 seconds. In typical embodiments, the first fluid may be delivered at a temperature of 65° C. for approximately 30-60 seconds, at 70° C. for approximately 5-45 seconds, at 75° C. for approximately 3-40 seconds, at 80° C. for approximately 3-30 seconds, or at 90° C. for approximately 3-20 seconds. The second fluid is typically delivered at a temperature at or below 37° C. for at least 15 seconds.

A time-varying application of heat is expected to have several advantages including but not limited to: differences between the frequency, phase and amplitude of the temperature waveforms measured at two or more locations (e.g. at the balloon's surface and at a location upstream of the balloon) may be indicative of the progress of thermal ablation and therefore offer a means of monitoring ablation in real-time; continuous modulation of the peak temperature offers a means of incrementally approaching thermal ablation without the need to inflate and deflate the balloon repetitively, thereby enhancing the precision of the treatment without prolonging the treatment time; continuous modulation of the peak temperature permits the application of elevated temperatures during well-controlled periods of short duration, which may help to ensure that the inner-most tissue layer is effectively ablated by the temperature peaks while simultaneously ensuring that the tissue sub-strata can dissipate heat in the time between peaks; the peak surface temperature may be ramped up or down in the course of modulation, so that a peak ablation temperature may be approached incrementally; and combinations of these.

In this embodiment, the temperature of balloon 120 surface may be held substantially constant for the duration of the application time at a selected value, and the resulting quasi-steady-state heat transfer profile into and through the target tissue is such as to locate the damage threshold of the target tissue at or near the intended boundary for treatment. The surface temperature is preferably of a value that is slightly higher than the threshold for damage, e.g. at or above 43° C., typically between 45° C. and 50° C., so that ablation is limited to the inner-most layer of the tissue while the deeper layers are undamaged, such as by maintaining the non-target tissue at a temperature below a necrotic threshold, such as by using the perfusion of blood as a heat sink.

A complete target tissue treatment cycle may comprise the rapid inflation of an empty or deflated balloon with hot fluid so as to establish uniform and positive contact between the balloon and the target tissue; the maintenance of constant and uniform temperature at the surface of the balloon by means of continuous mixing of the contents of the balloon in conjunction with the continuous adjustment of the heat flow into and out of the balloon, applied over a time sufficient to establish quasi-steady-state heat transfer; followed by rapid deflation of the balloon so as to disengage the balloon from contact with the target tissue and/or rapid insufflation to radially expand the target tissue (e.g. to stop energy transfer). In some embodiments, one or several repeat cycles may be applied to one or more discrete portions of the target tissue to effect complete treatment of all target tissue intended to be treated. In one embodiment, inflation of a treatment element is accomplished in less than 10 seconds from initiation of expansion, typically less than 5 seconds. In another embodiment, deflation of the treatment element and/or radial expansion of the target tissue using insufflation (as described hereabove), such as to remove contact between the target tissue and the treatment element sufficient to eliminate heat transfer, is accomplished in less than 10 seconds, typically less than 5 seconds.

Ports 161, 162 and 163, and each of the other inflow and outflow ports of the present inventive concepts, may each be configured to deliver fluid to balloon 120 and/or to extract fluid from balloon 120. In some embodiments, during single or multiple tissue treatments, ports 161, 162 and/or 163 are configured to deliver fluid for a first time period, and extract fluid for a second time period. In one embodiment, a pump or negative pressure source is provided to perform a negative pressure priming procedure, defined herein as a procedure to remove a majority of fluid from lumen 160, lumen 113 and/or balloon 120, such as to remove non-ablative temperature fluid and/or gas bubbles. A negative pressure priming procedure may be performed prior to delivering a thermal dose comprising fluid at an elevated temperature such as a temperature above 65° C.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 3:
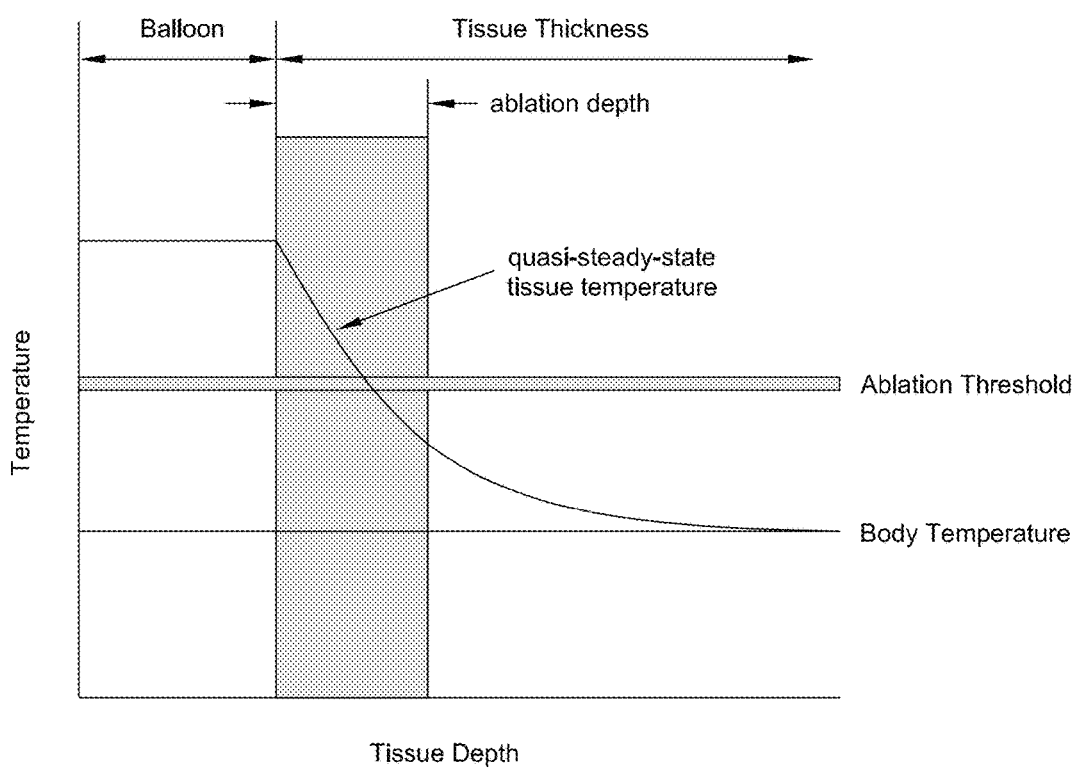
FIG. 3 is a quasi-steady-state temperature profile generated using the ablation device of FIG. 2, consistent with the present inventive concepts.

FIG. 3 illustrates a quasi-steady-state temperature profile generated using the ablation device described in reference to FIG. 2, in accordance with the present inventive concepts. The illustrated temperature profile is established within a cross-section of the target tissue, such as the wall of a hollow organ such as the duodenum, when the target tissue is assumed to be in efficient thermal contact with a balloon or other treatment element that is filled with a hot-fluid. The general form of the temperature profile is illustrative for a hot-fluid balloon that is configured to have a time-invariant surface temperature. The temperature profile is herein described as quasi-steady-state, rather than strictly steady-state, because it is to be understood that the temperature profile is expected to be slowly and systematically varying, and that the variation is substantially due to the progress of ablation and the associated changes in local perfusion and heat transfer that accompany ablation.

Figure 4A:
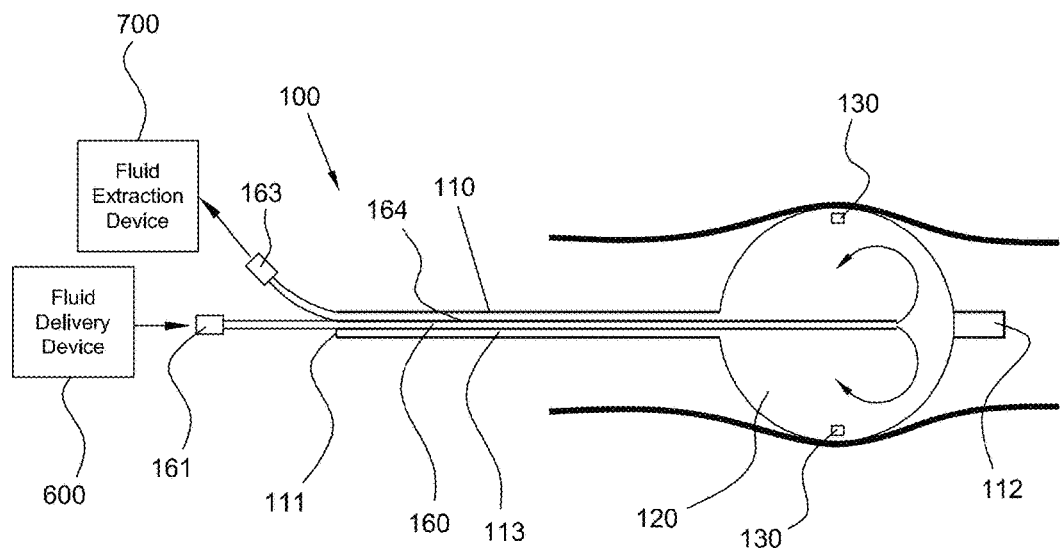
FIGS. 4A and 4B are side views of an ablation device positioned in a body lumen, shown with two directions of hot fluid delivery, consistent with the present inventive concepts.
Figure 4B:
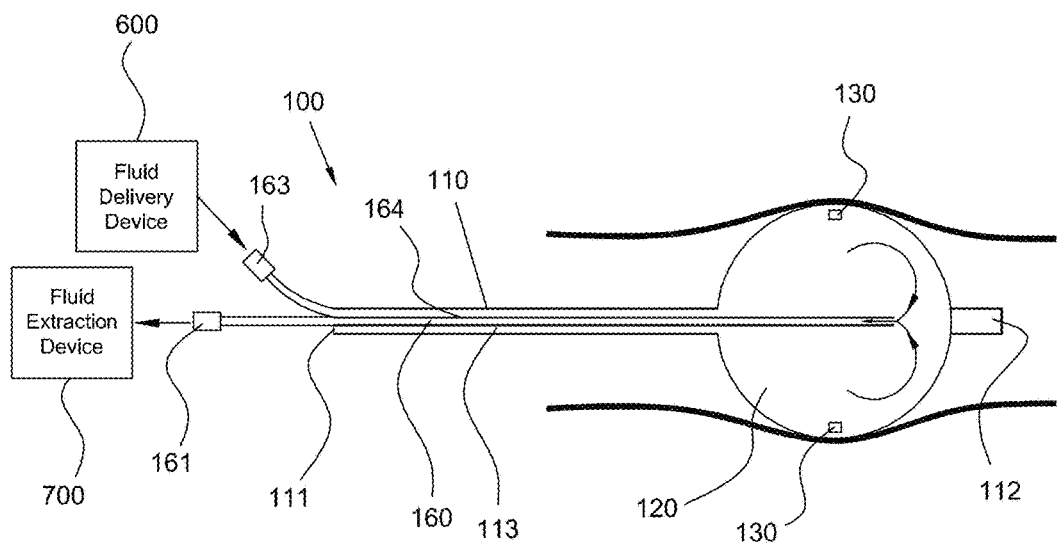

FIGS. 4A and 4B illustrate a device for treating tissue, positioned in a body lumen and including an inner lumen and an outer lumen for delivering or removing hot fluid from a balloon, in accordance with the present inventive concepts. Device 100 includes a proximal end 111, a distal tip 112 and a shaft 110. Shaft 110 includes a lumen 113 therethrough. Lumen 113 is in fluid communication with port 163. Port 163 is attached to a fluid transfer device, such as a fluid delivery device configured to deliver temperature controlled fluid to lumen 113 or a fluid extraction device configured to remove fluid from lumen 113. Residing within lumen 113 is shaft 164 which comprises lumen 160 therethrough. Lumen 160 is fluidly attached to port 161. Port 161 is similarly configured to be attached to a fluid transfer device, such as a fluid delivery device configured to deliver temperature controlled fluid to lumen 160 or a fluid extraction device configured to remove fluid from lumen 160. Typical fluid delivery and extraction devices are described in reference to FIG. 19 herebelow and are configured to independently deliver and remove fluid from lumens 113 and 160. Device 100 also includes balloon 120 which is configured to be inflated by fluids delivered through lumens 113 and 160 such that balloon 120 contacts target tissue and enables treatment of the target tissue via these fluids. In the embodiment of FIG. 4A, port 161 is attached to fluid delivery device 600, typically a pump or pressurized reservoir configured such that fluid flows from lumen 160 into balloon 120. Port 163 is attached to fluid extraction device 700, such as a pump or reservoir maintained at a vacuum or other negative pressure sufficient to cause fluid to flow from balloon 120 into lumen 113 and out port 163. Negative pressures can be applied to port 163 by fluid extraction device 700 such that the flow from balloon 120 into lumen 113 and out port 163 is at a higher level than would otherwise have been achieved if port 163 was simply open to or otherwise maintained at room pressure. In an alternative embodiment, fluid extraction device 700 creates a pressure above room pressure but at a level low enough to cause fluid to flow from balloon 120 into lumen 113 and out port 163 (e.g. at a pressure level below the level of fluid introduced by fluid delivery device 600). In the embodiment of FIG. 4B, the connections are reversed, and port 163 is attached to fluid delivery device 600 and port 161 is attached to fluid extraction device 700. Fluid flows from port 163 through lumen 113 and into balloon 120. Fluid flows from balloon 120, into lumen 160 and out port 161, as is described in the reverse direction in reference to FIG. 4A hereabove. In an alternative embodiment, a fluid extraction device 700 is not included, such that port 163 of FIG. 4A or port 161 of FIG. 4B is simply unattached to any device or otherwise connected to a reservoir at a pressure approximating room pressure, such that rate of fluid transferred through balloon 120 is controlled by the fluid delivery device. Inclusion of fluid extraction device 700 allows increased flow of fluid through balloon 120 (e.g. when fluid extraction device 700 is operated at a negative pressure), as well as increased precision of control of fluid flow (e.g. by controlling the pressure differential applied between lumen 113 and lumen 160. It will be understood that the arrangement of lumens 113 and 160 may be concentric, as shown in FIGS. 4A and 4B, may be side-by-side, or may be any other arrangement that provides for the fluid communication to and/or from balloon 120. One or more of lumens 113 and/or 160 may be reinforced, such as when shaft 110 and/or shaft 164, respectively, comprise a reinforced shaft such as a braided or spiral-wire reinforced tube configured to prevent collapse during vacuum or other negative pressure level states. Referring to the embodiment of FIG. 4A, both fast thermal rise-time and fast thermal response-time may be achieved for the hot fluid in balloon 120 by delivering fluid at a positive pressure via lumen 160 (e.g. delivering hot fluid through lumen 160) while extracting fluid by applying a negative pressure via lumen 113 (e.g. applying a negative pressure or otherwise withdrawing fluid through lumen 113). The simultaneous delivery and withdrawal of fluid maximizes the differential pressure across balloon 120 and enables high flow rate of fluids through balloon 120. Referring to the embodiment of FIG. 4B, both fast thermal rise-time and fast thermal response-time are achieved for the hot fluid in balloon 120 by applying a positive pressure via lumen 113 (e.g. delivering hot fluid through lumen 113) while applying a negative pressure via lumen 160 (e.g. applying a negative pressure or otherwise withdrawing fluid through lumen 160). In some embodiments, a purging procedure may be performed prior to the introduction of a hot fluid thermal dose into balloon 120, such as a purging with a fluid such as air. Alternatively or additionally, a negative pressure priming procedure, as has been described hereabove, may be performed, such as to reduce or eliminate gas bubbles or to remove a fluid at an undesired temperature. Purging and/or negative pressure priming procedures may be applied to one or more fluid pathways of device 100 including but not limited to: lumen 160, lumen 113 and/or balloon 120. In some embodiments, balloon 120 may be configured to cool tissue, such as a cooling procedure performed prior to and/or after the application of a thermal dose, as is described in reference to FIG. 18 hereinbelow.

Thermal rise-time is defined herein as the time duration to reach target temperature within and/or on the surface of balloon 120 from the start of the inflation period. In a typical embodiment, thermal rise-time is rapid, such as a thermal rise time in which fluid temperature reaches 90% of a target temperature within 5 seconds of initiating the inflation. Thermal response-time is defined herein as the time duration to reach and maintain an adjusted target temperature within and/or on the surface of balloon 120. In a typical embodiment, thermal response time is rapid, such as a thermal response time in which fluid temperature reaches 90% of a modified target temperature within 15 seconds of initiating the change to the new target temperature. In some embodiments, thermal fall-time is also rapid, such as a thermal fall time in which fluid temperature reaches 110% of body temperature with 15 seconds, typically less than 5 seconds.

Thermal rise-time may be affected by whether balloon 120 is in contact with tissue, the amount of contact, and the temperature of the tissue being contacted. Filling of balloon 120 that causes or changes contact with tissue will impact thermal rise-time, such as to slow down thermal rise time as contact initiates and/or increases. Thermal rise times may be improved by purging one or more fluid pathways of device 100 with air prior to delivery of hot fluid. Thermal rise times may be improved by applying a vacuum or other negative pressure to port 163 during delivery of hot fluid via port 161.

Thermal fall-time may be configured to correlate to the time it takes balloon 120 to reach a temperature that no longer delivers significant energy to the target tissue. A balloon 120 whose temperature falls below target temperature, for example 5° C., 10° C. and/or 20° C. less than a target temperature, may be considered to have stopped ablating tissue. Thermal fall times may be improved by purging with air and/or cold fluid after cessation of the target tissue treatment, such as by applying a vacuum or other negative pressure to port 163 and/or delivering cold fluid via port 161, respectively.

In one embodiment, the adjustment of temperature is maintained by one or more temperature controlling elements that may be used to alter the heat flux passing into and out of balloon 120, including external and internal heat sources such as resistance heaters, as well as various elements for controlling fluid flow rate such as pumps, positive pressure sources and negative pressure sources. Heaters of various sorts rely on convective heat transfer; therefore their performance is enhanced by high fluid flow rates. A fast thermal rise-time is advantageous for several reasons including but not limited to: the total treatment time may be reduced, thus minimizing risk and discomfort and cost to the patient; a shorter rise-time reduces variability in the treatment time and so permits more precise control of the overall thermal dose; and combinations of these. Fast thermal response-time is advantageous because it enables rapid and precise adjustments in balloon temperature in response to fluctuations measured by temperature sensor 130 within balloon 120, which also improves precision in the control of the overall thermal dose. Fast thermal fall-times provide advantages as well, such as to achieve a precise depth of ablation. The ability to stop transfer of heat to tissue can be achieved by a fast thermal fall-time. Alternatively or additionally, a device including a treatment element which can be rapidly moved away from tissue (e.g. via balloon 120 radial compression and/or target tissue radial expansion) can be used to quickly stop treatment of the target tissue. While heat is transferred from balloon 120 to target tissue, heat is also being conducted from target tissue to non-target tissue structures. Rapid thermal rise and fall times can be used to minimize amount of undesired heat transferred to non-target tissue, such as to achieve a shallow thermal gradient during treatment.

In the embodiments shown in FIGS. 4A and 4B, differential pressure is maximized by simultaneously applying a positive fluid pressure to port 163 and a negative pressure (e.g. suction) to port 161, or vice versa, each of which is in fluid communication with balloon 120. While the differential pressure across balloon 120 is maintained at a high level, and while the resulting fluid flow rate is also maintained at a high level, the pressure within balloon 120 may be maintained at a much lower level than would be achieved with a single positive or negative pressure source (e.g. fluid delivery device 600 alone). Precise and dual source adjustment of balloon 120 pressure is advantageous for several reasons, including but not limited to: the minimum pressure required to establish uniform and positive contact between the balloon and the target tissue may vary from location to location within an organ and therefore is preferably an independent control variable which can be adjusted as required to optimize the ablation process during the treatment; the safety of the overall treatment may be improved by minimizing the balloon pressure; and combinations of these.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 5:
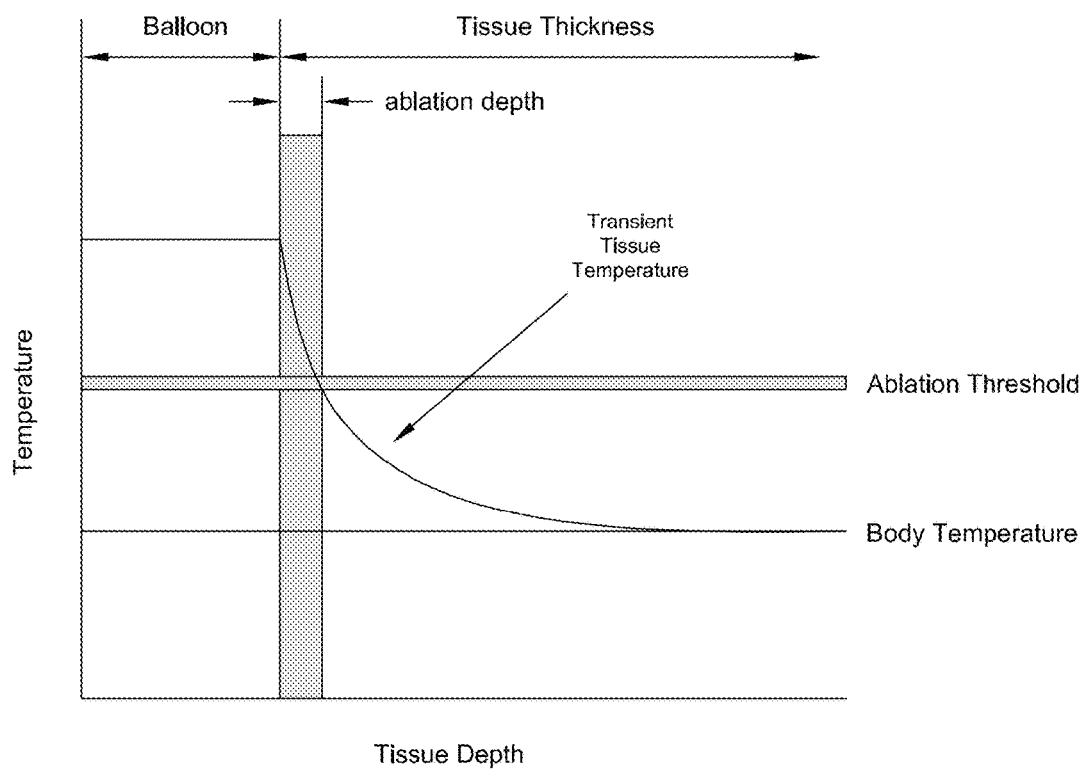
FIG. 5 is a transient tissue temperature profile generated using the device described in reference to FIGS. 4A and 4B, consistent with the present inventive concepts.

FIG. 5 illustrates a transient tissue temperature profile generated using an ablation device as is described in reference to FIGS. 4A and 4B hereabove, in accordance with the present inventive concepts. In one embodiment, the thermal dose required to limit ablation to a thin inner layer of target tissue (e.g. a layer comprising at least the full mucosal thickness of the duodenum) is achieved by means of a precisely controlled application of a hot fluid balloon operating at a time-average temperature over a well-controlled time interval. In this embodiment, the time interval during which heat is applied to the target tissue is understood to be shorter than would be required to achieve a quasi-steady-state temperature profile, as described and shown in FIG. 3 hereabove, within and across the target tissue cross-section. Therefore, the temperature profile is transient and the location of the boundary for necrosis within the tissue cross-section is a strong function of time and temperature such that both parameters must be controlled with precision in order to limit necrosis to a thin inner layer of the target organ.

Figure 6A:
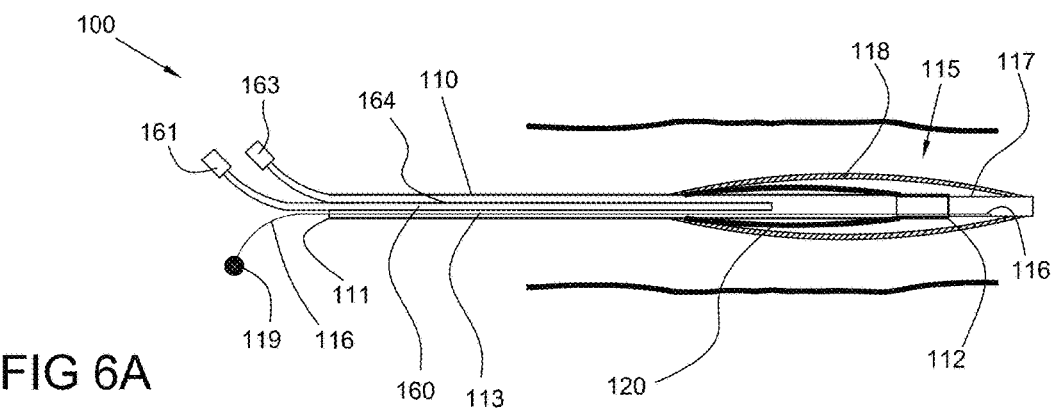
FIGS. 6A, 6B and 6C are side views of an ablation device positioned in a body lumen, shown in unexpanded, partially expanded and fully expanded views, respectively, consistent with the present inventive concepts.
Figure 6B:
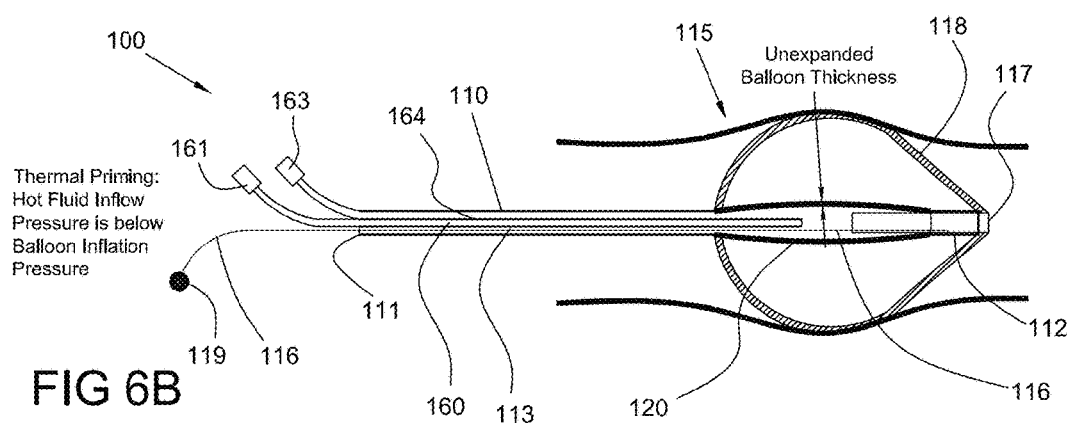
Figure 6C:
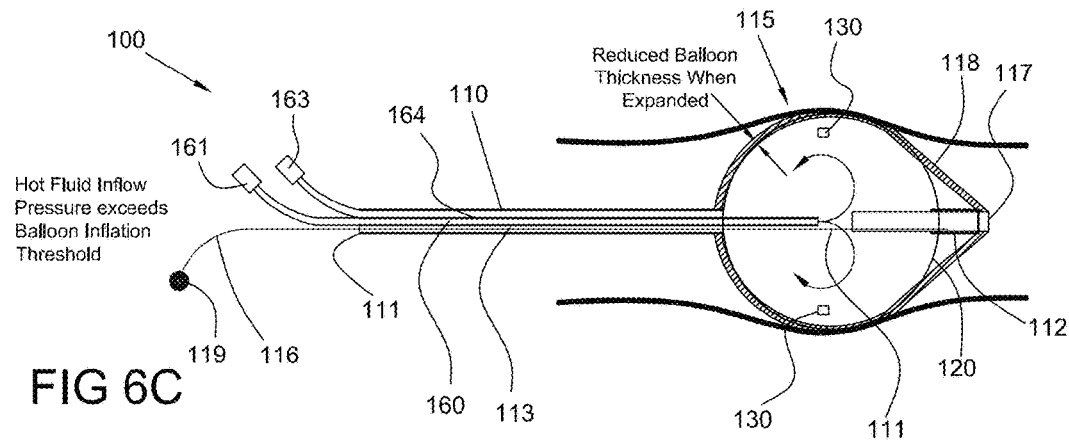
Figure 6D:
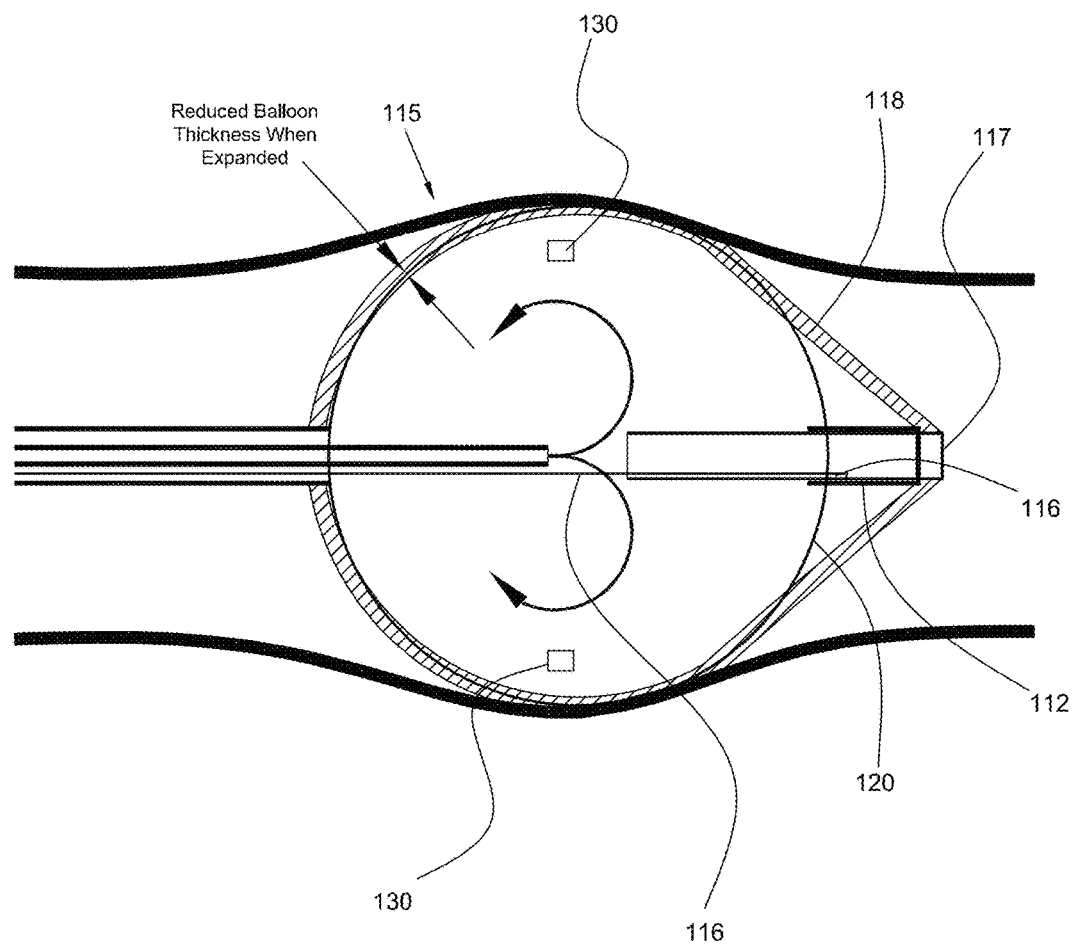
FIG. 6D provides a magnified view of the distal portion of the ablation device of FIG. 6C, consistent with the present inventive concepts.

FIGS. 6A-6C, illustrate a device for treating tissue, positioned in a body lumen and including an expandable element, shown in unexpanded, partially expanded, and fully expanded states, respectively, in accordance with the present inventive concepts. FIG. 6D illustrates a magnified view of the distal portion of the device of FIG. 6C. Device 100 is of similar construction, and includes components similar to device 100 of FIGS. 4A and 4B. Device 100 further includes a positioning assembly 115 configured to position the treatment element, balloon 120, relative to tissue, such as target tissue and/or non-target tissue. The positioning assembly comprises an expandable cage 118 which is attached to deployment shaft 116 and a floating tube 117. The proximal end of shaft 116 includes grip 119, configured as a grip point for an operator to advance and/or retract shaft 116. Floating tube 117 is slidingly received by device 100 distal portion 112. Advancement of shaft 116 causes floating tube 117 to move distally and expandable cage 118 to elongate and radially compress, as shown in FIG. 6A. Retraction of shaft 116 causes floating tube 117 to move proximally and expandable cage 118 to shorten and radially expand, as shown in FIGS. 6B, 6C and 6D. Positioning assembly 115 may be configured to position an expandable treatment element, such as balloon 120, in its expanded and/or unexpanded states, in the center of a body lumen (as shown) or at an off-center location. Positioning assembly 115 may be configured to move a treatment element, such as balloon 120, in a partially expanded or unexpanded state, away from tissue, such as a rapid movement occurring in less than 5 seconds, typically less than 1 second, such as to prevent continued transfer of energy from balloon 120 to tissue. While positioning assembly 115 of FIGS. 6A-6C comprises an expandable cage, numerous radially deployable mechanisms could be employed to position a treatment element relative to tissue, such as expandable balloons, radially deployable arms, and the like. Expandable cage 118 and/or other positioning elements of positioning assembly 115 may be placed at the same longitudinal location as balloon 120 (as shown, in FIGS. 6A-C), or at a location proximal and/or distal to balloon 120. In some embodiments, expandable cage 118 is configured to move tissue away from balloon 120 (e.g. to further expand from the configuration shown in FIG. 6D), such as to stop delivery of energy to tissue. Positioning assembly 115 may be integral to device 100 (as shown in FIGS. 6A-6D), or it may be a separate device configured to position a treatment element, such as balloon 120, relative to tissue, such as target or non-target tissue.

Device 100 may be configured to allow thermal priming to be performed on balloon 120, where thermal priming is defined as the process of pre-heating at least a portion of balloon 120 material and/or the conduits leading to balloon 120, as has been described in detail hereabove. The pre-heating is typically performed prior to balloon 120 inflation, such as to heat fluid transport conduits including lumen 113 and/or lumen 160. Thermal priming may be accomplished by delivering fluid at an elevated temperature while preventing the pressure in balloon 120 from exceeding a threshold, such as a threshold which would cause expansion of balloon 120 (i.e. prior to initiation of a thermal dose such as while preventing balloon 120 from contacting tissue). Delivery of fluid below this threshold pressure accommodates thermal priming because it permits the circulation of hot fluid through lumen 113 and/or lumen 160, and through balloon 120 itself, prior to inflation of balloon 120, as is shown in FIG. 6A. This pre-heated condition of balloon 120, as well as lumens 113 and/or 160, ensures a fast thermal rise-time when the balloon is eventually inflated, due to the minimization of heat loss to these components. As a consequence of thermal priming, the inflation fluid will enter balloon 120 at or near the intended temperature for initial treatment, as balloon 120 reaches an inflated state shown in FIG. 6C. FIG. 6D illustrates a magnified view of the distal portion of device 100 of FIG. 6C.

Figure 7:
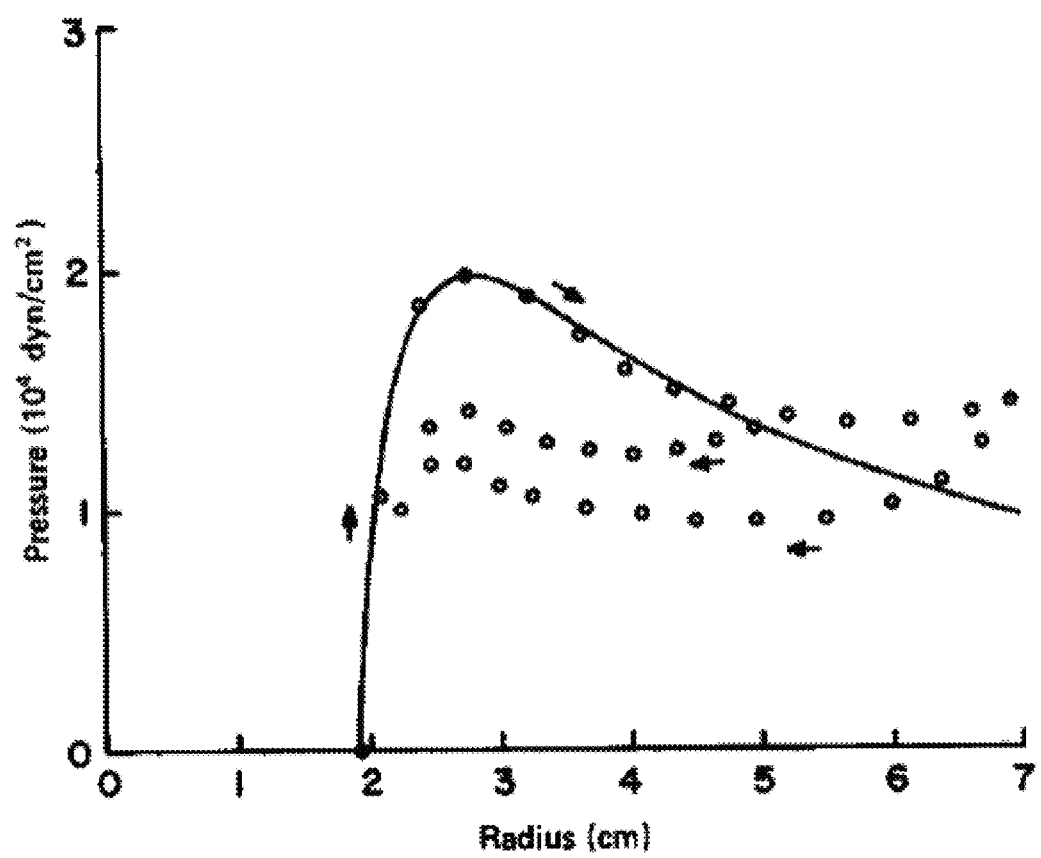
FIG. 7 is a graph of pressure curves for an expandable balloon, consistent with the present inventive concepts.

In one embodiment, a pressure threshold for inflation is achieved by balloon 120's materials of construction, as well as thickness and other chosen geometric parameters. For example, balloon 120 can be designed to have a force-stretch diagram similar to the one shown in FIG. 7. Suitable balloon materials include but are not limited to: silicone rubber; latex; neoprene; polyurethane; polyester; and combinations of these. In some embodiments, one or more balloon's 120 comprises polyethylene terephthalate (PET). For a given material, balloon 120 wall thicknesses are selected to be thick enough to substantially resist inflation at or below a pressure threshold. Alternatively or additionally, one or more ribs may be included on or within balloon 120, not shown but comprising balloon material or other material and configured to resist expansion of balloon 120. The pre-inflation shape of balloon 120 comprises a reduced diameter shape such as to remain separated or otherwise thermally disengaged from the target tissue. For example, a balloon 120 exhibiting a pressure threshold for inflation may be designed to have a substantially cylindrical shape and composed of silicone rubber with 3 mm inside diameter and 1 mm wall thickness. Such a balloon 120 will resist inflation until a pressure threshold is reached. Below the pressure threshold, balloon 120's diameter and wall thickness will remain substantially unchanged, even as hot fluid flows through balloon 120. If such a balloon 120 is situated inside tubular target tissue with an inside diameter of 10 mm, for example, then heat transfer to the target tissue is minimized because balloon 120 remains physically disengaged from the target tissue and because the thick wall of balloon 120 and the space between balloon 120 and the target tissue behaves as a thermal insulator. As the balloon 120 pressure is increased beyond the pressure threshold for inflation, balloon 120 diameter increases to establish uniform and positive contact between balloon 120 and the target tissue. Simultaneous with expansion, the wall of balloon 120 becomes thinner. Both of these conditions initiate and/or otherwise improve heat transfer to the target tissue.

As shown in FIG. 6C, expandable cage 118 is expanded and balloon 120 is in an inflated state. Once the pressure threshold is exceeded and balloon 120 is inflated, higher fluid flow rates may be sustained without over-inflating balloon 120. As has been noted above in reference to FIGS. 4A and 4B, higher flow rates result in fast thermal-response time and greater precision in temperature control. Higher fluid flow rates may be sustained since the inflow pressure to balloon 120 for a given inflation diameter is increased by the amount of the pressure threshold, thus increasing the differential pressure across balloon 120.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figures 8, 8A:
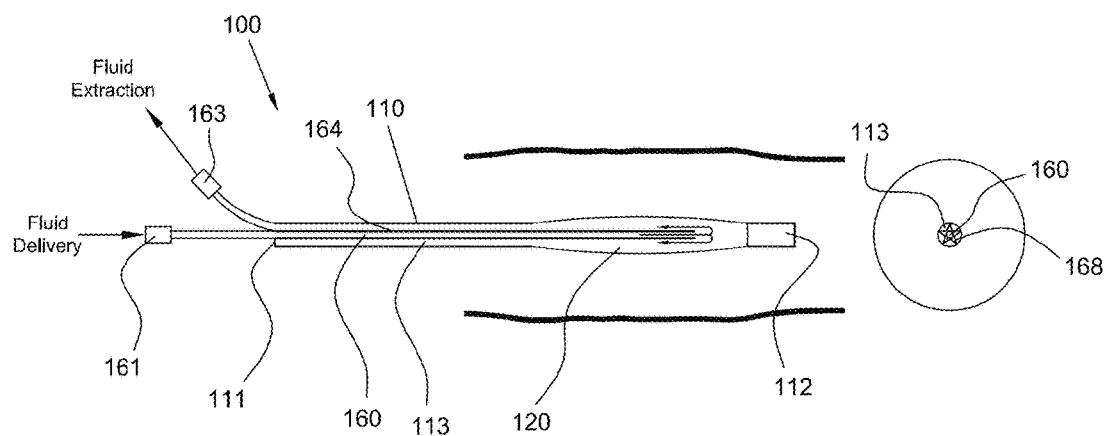
FIG. 8 is a side view of an ablation device positioned in a body lumen, the ablation device comprising an element to prevent luminal collapse, consistent with the present inventive concepts.
FIG. 8A is an end sectional view of the device of FIG. 8, consistent with the present inventive concepts.

FIG. 8 illustrates a device for treating tissue, positioned in a body lumen and including an element to prevent luminal collapse, in accordance with the present inventive concepts. FIG. 8A illustrates a cross-sectional view of the device of FIG. 8. Device 100 is of similar construction, and includes components similar to device 100 of FIGS. 4A and 4B. In the embodiment illustrated in FIGS. 8A and 8B, thermal priming is accomplished by sustaining a flow through balloon 120 while port 163 is held at negative internal pressure relative to the pressure of a heated fluid, entering lumen 160 via port 161. In this embodiment, balloon 120 is structured so as to permit flow of hot fluid through balloon 120 when it is in its deflated state, as described in reference to FIGS. 6A and 6B hereabove. As is shown in FIG. 8A, balloon 120 may include one or more support structures, such as flutes 168, which may be constructed and arranged to prevent collapse of balloon 120 and/or lumen 160, such as during a period in which balloon 120 and/or lumen 160 is at a low or negative pressure. Alternative or in addition to flutes 168, other support elements may be included such as a support element selected from the group consisting of: a helical coil; a strut; a wire; a wire-form structure; a tube; a foam member; a spring; and combinations of these.

Device 100 typically includes at least one temperature sensor, such as sensor 130 described herein, constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figures 9, 9A:
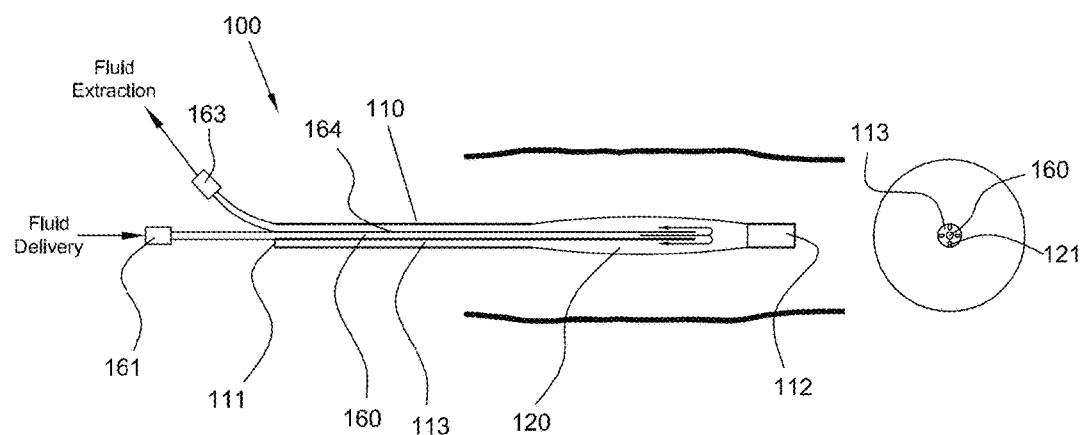
FIG. 9 is a side view of an ablation device positioned in a body lumen, the ablation device comprising an element to prevent luminal collapse, consistent with the present inventive concepts.
FIG. 9A is an end sectional view of the device of FIG. 9, consistent with the present inventive concepts.

FIG. 9 illustrates a device for treating tissue, positioned in a body lumen and including an element to prevent luminal collapse, in accordance with the present inventive concepts. FIG. 9A illustrates a cross-sectional view of the device of FIG. 9. Device 100 is of similar construction, and includes components similar to device 100 of FIGS. 8 and 8A. Device 100 of FIGS. 9 and 9A includes structures that can be positioned within balloon 120 to provide means for flow despite the collapse of the balloon under low or negative pressures. Device 100 includes rib 121, which comprises an internal support structure embedded into the wall of balloon 120. Alternative or in additional to rib 121, a support element embedded in the wall of balloon 120 may comprise one or more support elements selected from the group consisting of: ridges; bumps; wire members; increased density portions; modified texture portions; and combinations of these. Ribs 121 and/or other support members may be constructed and arranged to maintain a flow of fluid into balloon 120 while balloon 120 is deflated or otherwise under low or negative pressure.

Device 100 typically includes at least one temperature sensor, such as sensor 130 described herein, constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 10A:
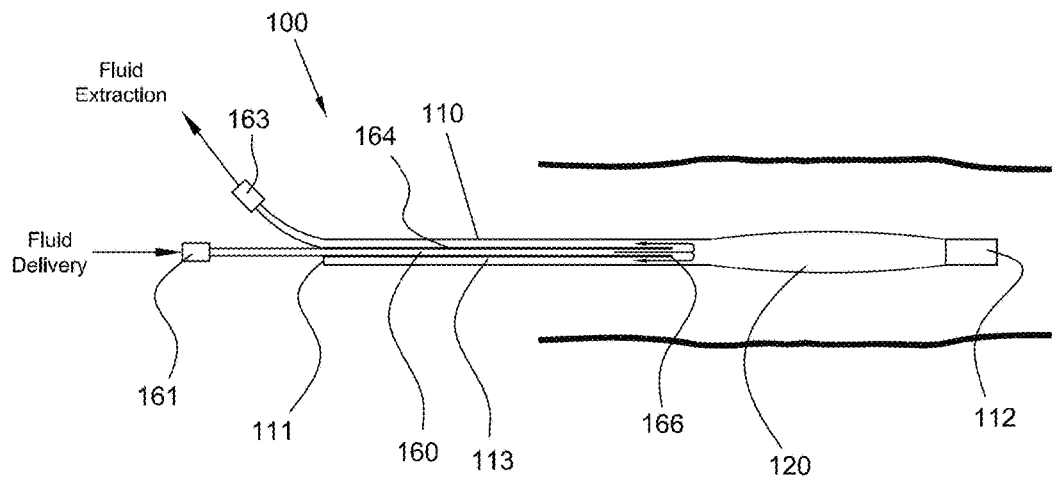
FIGS. 10A and 10B are side views of an ablation device positioned in a body lumen, the ablation device comprising a translatable shaft, shown in unexpanded and expanded states, respectively, consistent with the present inventive concepts.
Figure 10B:
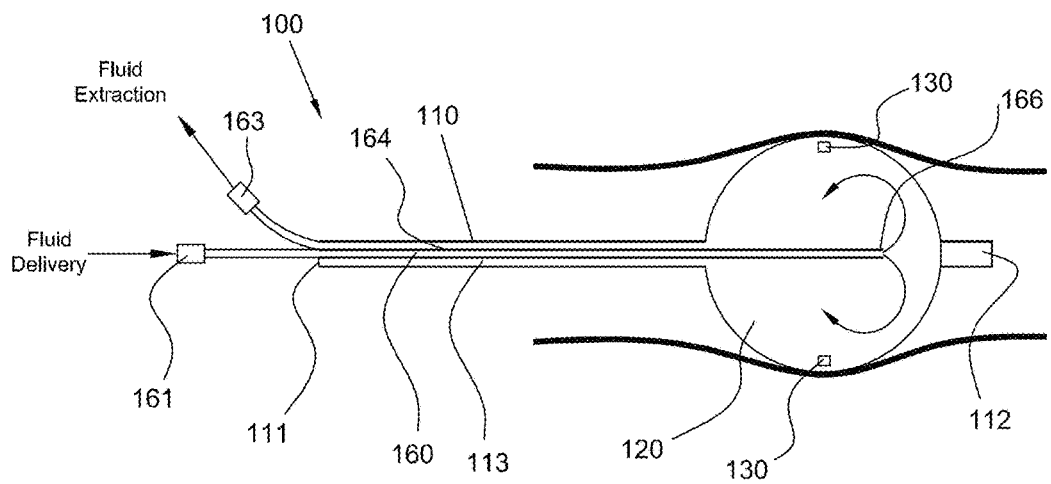

FIGS. 10A and 10B illustrate a device for treating tissue, positioned in a body lumen and including an expandable element, shown in deflated and inflated states, respectively, in accordance with the present inventive concepts. Device 100 is of similar construction, and includes components similar to device 100 of FIGS. 4A and 4B. In the embodiment illustrated in FIGS. 10A and 10B, shaft 164 can be translated forward and back within shaft 110. In the illustrated embodiment, thermal priming is accomplished by selectively and controllably routing a re-circulating flow of hot fluid so that it bypasses balloon 120. In this embodiment, thermal priming involves repositioning distal end 166 of shaft 164 from a position within balloon 120 to a position proximal to balloon 120, at a time prior to inflation of balloon 120. Priming fluid (e.g. fluid at an elevated temperature) is delivered via port 163 and/or 164, and removed via port 164 and/or 163 respectively, as is described hereabove.

As shown in FIG. 10B, at the completion of thermal priming, distal end 166 of shaft 164 is returned to a position within balloon 120 so that the existing pressure differential between inflow and outflow or a newly selected pressure differential (e.g. an increased pressure differential) results in the rapid inflation of balloon 120.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 11A:
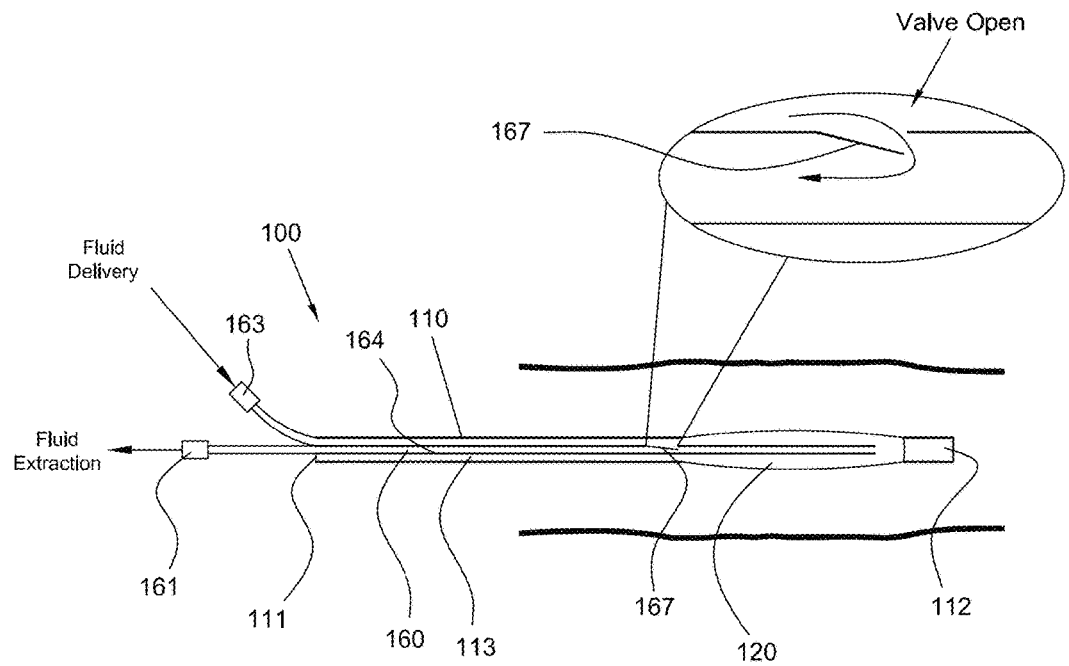
FIGS. 11A and 11B are side views of an ablation device positioned in a body lumen, the ablation device comprising a fluid delivery tube with a valve, shown in unexpanded and expanded states, respectively, consistent with the present inventive concepts.
Figure 11B:
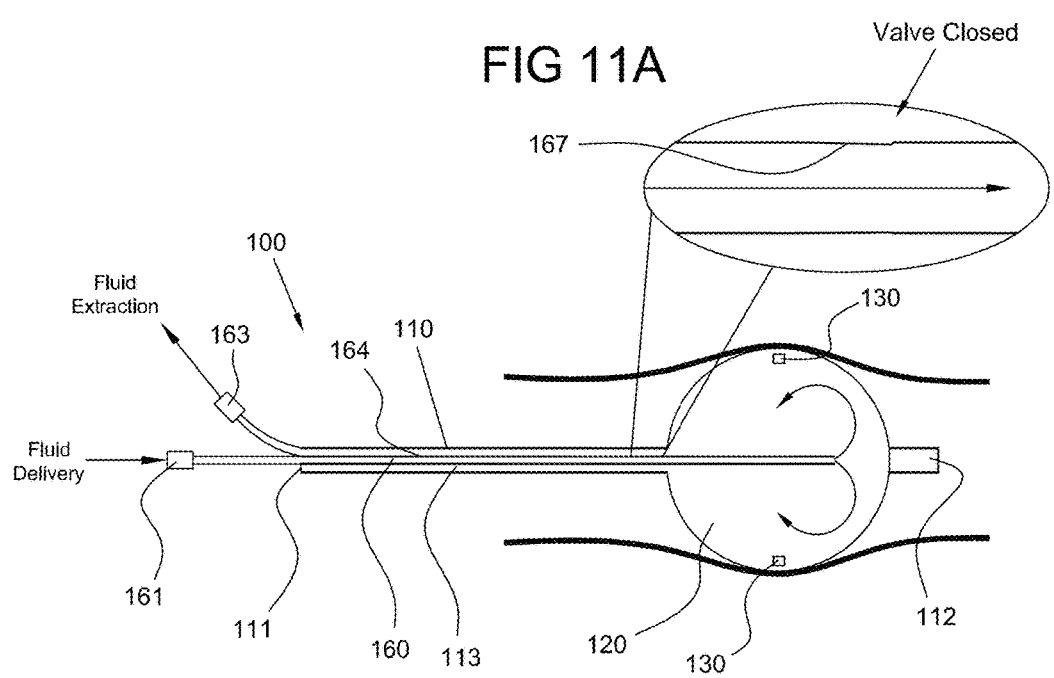

FIGS. 11A and 11B illustrate a device for treating tissue, positioned in a body lumen and including an expandable element, shown in deflated and inflated states, respectively, in accordance with the present inventive concepts. Device 100 is of similar construction, and includes components similar to device 100 of FIGS. 4A and 4B. In the embodiment illustrated in FIGS. 11A and 11B, shaft 164 includes a valve 167 positioned along its length and in fluid communication with lumen 160. Valve 167 typically comprises a flap-valve or other one-way valve construction. Valve 167 is oriented such that when negative pressure is applied to lumen 160, such as via suction applied to port 161, valve 167 opens and balloon 120 deflates. With the valve open, fluid introduced through lumen 113, such as via port 163, bypasses balloon 120, preventing its inflation, and travels proximally through lumen 160, as shown in FIG. 11A. In this configuration, thermal priming can be accomplished by delivering hot fluid through lumen 113. When a positive pressure is introduced into lumen 160, such as a positive pressure approximating a pressure applied to lumen 113, valve 167 is closed, allowing fluid introduced through port 163 to inflate balloon 120, as is shown in FIG. 11B. Valve 167 may comprise two or more valves, such as valves deployed in similar or dissimilar orientations, such as when fluid administered in a first direction causes thermal priming and fluid administered in the opposite direction causes expansion of balloon 120. In an alternative embodiment, valve 167 comprises a small diameter conduit between lumen 113 and lumen 160, such that thermal priming can be achieved if fluid is delivered at a rate below a threshold. When the threshold is exceeded, valve 167 provides sufficient resistance such that balloon 120 is expanded, such as an expansion to contact and treat target tissue.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 12A:
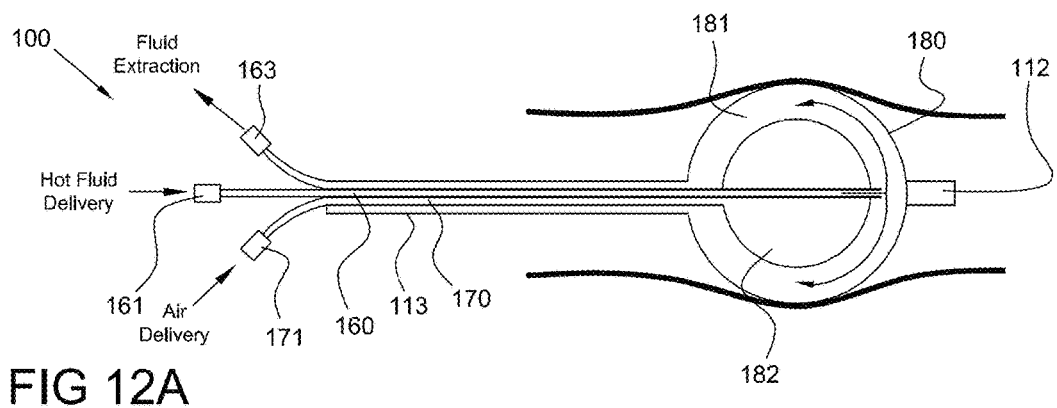
FIGS. 12A, 12B and 12C are side views of an ablation device positioned in a body lumen, the ablation device comprising a dual chamber balloon, shown in fully inflated, partially deflated, and fully deflated states, respectively, consistent with the present inventive concepts.
Figure 12B:
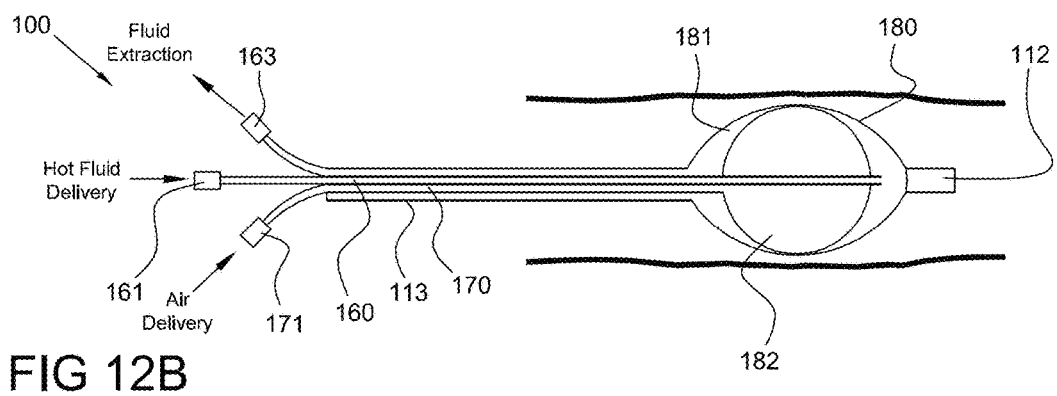
Figure 12C:
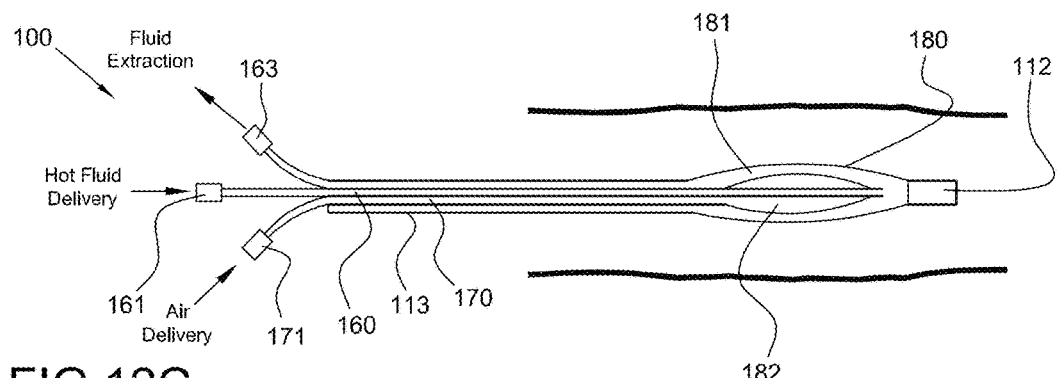

FIGS. 12A, 12B and 12C illustrate a device for treating tissue, positioned in a body lumen and including an expandable element, shown in an inflated, a partially inflated, and fully deflated states, respectively, in accordance with the present inventive concepts. Device 100 is of similar construction, and includes components similar to device 100 of FIGS. 4A and 4B. In the embodiment illustrated in FIGS. 12A and 12B, device 100 includes a multi-chamber balloon 180, comprising two or more separately inflatable chambers, outer chamber 181 and inner chamber 182. Chambers 181 and 182 are separated by a partition, typically made of material similar to material making up balloon 180. Chambers 181 and 182 may comprise one or more balloon materials described hereabove, such as elastic and inelastic materials, such as to create balloon structures that are compliant and/or non-compliant, or that expand after being pressurized above a pressure threshold (e.g. the pressure-thresholded balloons described hereabove). When inner chamber 182 is inflated, such as with air, the volume of hot fluid required to fill outer chamber 181 is less than a similarly sized balloon with a single chamber (i.e. without inner chamber 182). Referring specifically to FIG. 12A, a fluid (e.g. air) enters port 171, travels through lumen 170, and fills inner chamber 182. A similar or dissimilar fluid (e.g. hot water or hot saline) enters port 161, travels through lumen 160, and fills outer chamber 181. To deflate outer chamber 181, flow of fluid through lumen 160 is ceased and/or a negative pressure is applied to port 163, as is shown in FIG. 12B. Similarly, to deflate inner chamber 182, flow of fluid through lumen 170 is ceased and/or a negative pressure is applied to port 171, as is shown in FIG. 12C.

A reduction in the volume of the hot fluid within balloon 180 may be advantageous for several reasons including but not limited to: a reduced volume of re-circulating hot fluid within balloon 180 will have a shorter residence time within balloon 180, and in this dynamic system, residence time directly impacts response-time; a reduced volume of re-circulating hot fluid within balloon 180 will require a shorter inflation time which translates directly into a faster thermal rise-time; and combinations of these. It will be understood that one or more of chambers 181 and/or 182 of multi-lumen balloon 180 that are not inflated with a hot fluid may instead be inflated with air or other gases or liquids that are not heated but instead are used for the purposes of a combination of volume displacement and/or insulation.

In FIG. 12C, the inner chamber 182 has also been deflated, such as by applying a suction to port 171. The fully deflated configuration of FIG. 12C may be used to introduce device 100, such as introduction through an endoscope.

In device 100 of FIGS. 12A-12C, multi-lumen balloon 180 is constructed such that the functions of inflation/deflation and heat transfer may be assigned to different chambers of balloon 180. Rapid inflation and deflation of balloon 180 is effected by means of lumen 170 (in fluid communication with inner chamber 182, and lumens 160 and/or 113, each in fluid communication with outer chamber 181. Lumen 170 may be controllably inflated and deflated with a gas, such as air, or any fluid which has a low viscosity and therefore can be rapidly transferred into and out of inner chamber 182. Lumens 160 and 113 serve as conduits to deliver a heat source for ablation, such as a hot fluid that preferably has a high thermal conductivity and optionally a high heat capacity. In an alternative embodiment, an expandable assembly such as an expandable basket or radially expandable arms may be placed within inner chamber 182, such as to expand inner chamber 182 with or without the infusion of fluid into inner chamber 182.

This device of FIGS. 12A-12C may be advantageous for several reasons including but not limited to: separation of the functions of inflation/deflation and heat transfer permit the efficient selection of fluids for each, such as a fluid with appropriate mechanical properties (e.g. low viscosity) that is selected for the inflation/deflation function while a fluid with excellent thermal properties (e.g. high thermal conductivity) may be separately selected for the heat transfer function; the re-circulating flow of the heat transfer fluid may optionally remain uninterrupted during the inflation and deflation periods thus permitting a continual state of thermal readiness of the system between inflation cycles; and combinations of these. In some embodiments, inner chamber 182 may be filled with hot fluid, such as to treat target tissue such as when outer chamber 181 is deflated. In these embodiments, outer chamber 181 may be expanded to move target tissue away from inner chamber 182, such as to rapidly stop energy transfer between hot fluid in chamber 182 and target tissue.

It will be understood that multi-lumen balloon 180 may have more than two lumens or cavities, in which case the inflation/deflation functions and the heat transfer functions may be apportioned between those lumens in a variety of ways. It will also be understood that this embodiment may be implemented in conjunction with any of the additional embodiments disclosed herein, so that, for example, the heat transfer portion of this embodiment may involve a hot-fluid bolus rather than a re-circulating fluid, or a combination of bolus and re-circulating heat transfer may be delivered through multiple lumens in fluid communication with the multiple chambers.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 13:
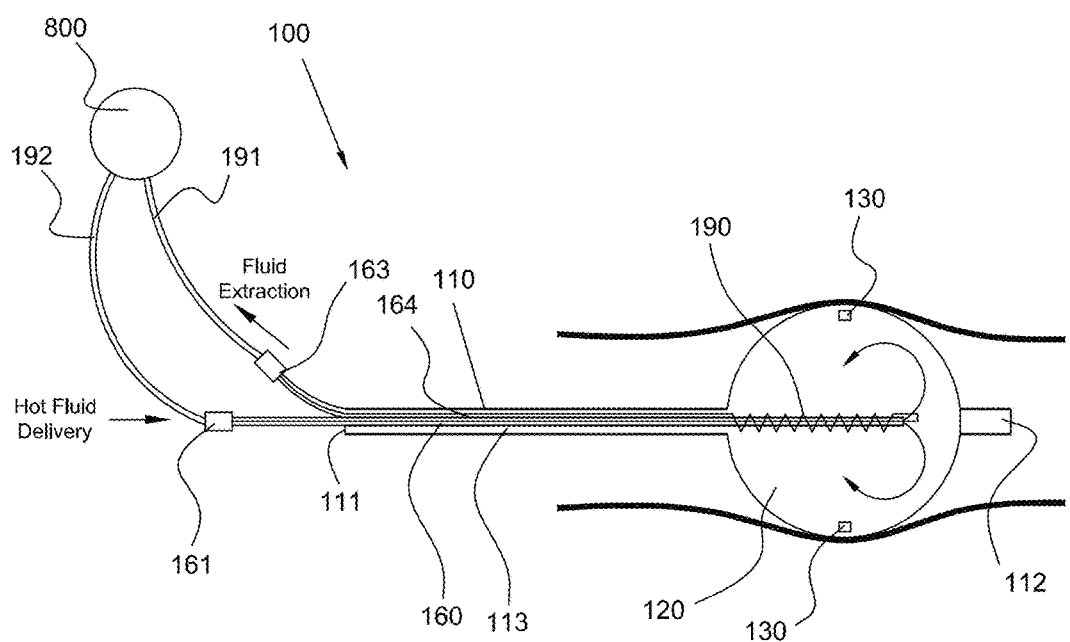
FIG. 13 is a side view of an ablation device positioned in a body lumen, the ablation device comprising a heater coil, consistent with the present inventive concepts.

FIG. 13 illustrates a device for treating tissue, positioned in a body lumen and including one or more fluid heating coils, in accordance with the present inventive concepts. Device 100 is of similar construction, and includes components similar to device 100 of FIGS. 4A and 4B. In the embodiment illustrated in FIG. 13, both fast thermal rise-time and fast thermal response-time are accomplished by having fluid re-circulating through lumens 160 and 113 passing through heater coil 190. Additionally or alternatively, one or more heat emitters may be situated within balloon 120 and/or within lumens 160 and/or 113. Coil 190 may be controllably operated by external means, such as controller 360 and/or EDU 330 described in reference to FIG. 19 herebelow. Alternative heat emitters include but are not limited to: resistance heaters, optical absorbers, ultrasound emitters, or any other means of dissipating energy into the fluid stream. It will be understood that a number of means of conveying energy to remote locations within shaft 110 may be employed, including but not limited to electrical wires, optical fibers, acoustic waveguides and the like. Device 100 includes fluid transport mechanism 800, which is configured both to deliver fluid to balloon 120 via port 161 and lumen 160 as well as extract fluid from balloon 120 via port 163 and lumen 113, via conduits 192 and 191, respectively. Fluid transport mechanism 800 may include a heat exchanger or other heating element, such as in addition to heater coil 190 or as an alternative. In one embodiment, fluid transport mechanism 800 comprises a single pumping assembly. In some embodiments, fluid transport mechanism 800 comprises a peristaltic or other pump configured to continuously deliver and extract fluid with a single rotational drive element. The single rotational drive element may comprise one or more of: a rotating impeller; a reciprocating volumetric displacement element; one or more rollers configured to drive fluid through tubing with peristalsis; and combinations of these.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 14:
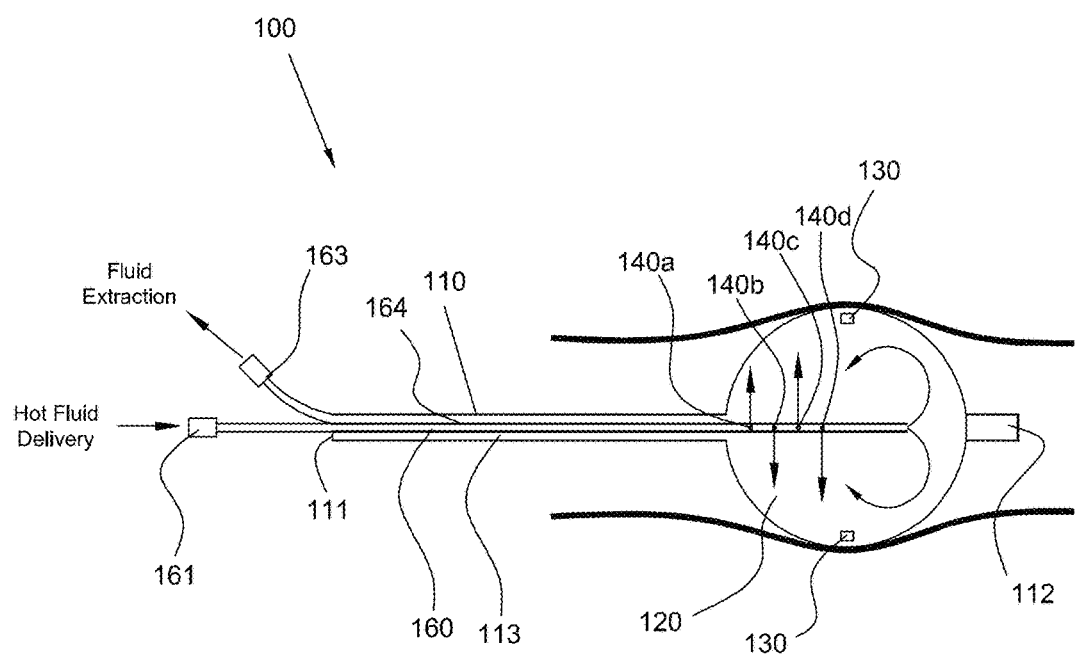
FIG. 14 is a side view of an ablation device positioned in a body lumen, the ablation device comprising multiple nozzles for directing flow of heated fluid, consistent with the present inventive concepts.

FIG. 14 illustrates a device for treating tissue, positioned in a body lumen and including multiple fluid directing nozzles, in accordance with the present inventive concepts. Device 100 is of similar construction, and includes components similar to device 100 of FIGS. 4A and 4B. In the embodiment illustrated in FIG. 14, uniform temperature within balloon 120 and along its surface may be accomplished by means of the dynamic mixing of hot fluid, such as within or proximal to balloon 120. For example, at least one nozzle can be situated along lumen 160 either within or leading to balloon 120. As shown, four nozzles 140a-d have the effect of accelerating the fluid as it flows through lumen 160, resulting in a jetting action that serves to agitate the fluid body and so eliminate hotter or cooler zones or "dead zones" within balloon 120. Nozzles 140a-d may be configured as constrictions, small holes, or ports, and may be shaped to achieve a particular mixing profile. In the embodiment shown in FIG. 14, fluid is delivered through port 161 such that it enters balloon 120 via nozzles 140a-d and the distal end of lumen 160. In an alternative embodiment, fluid may be delivered to balloon 120 via lumen 113, and extracted from balloon 120 via lumens 160 and nozzles 140a-d.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 15:
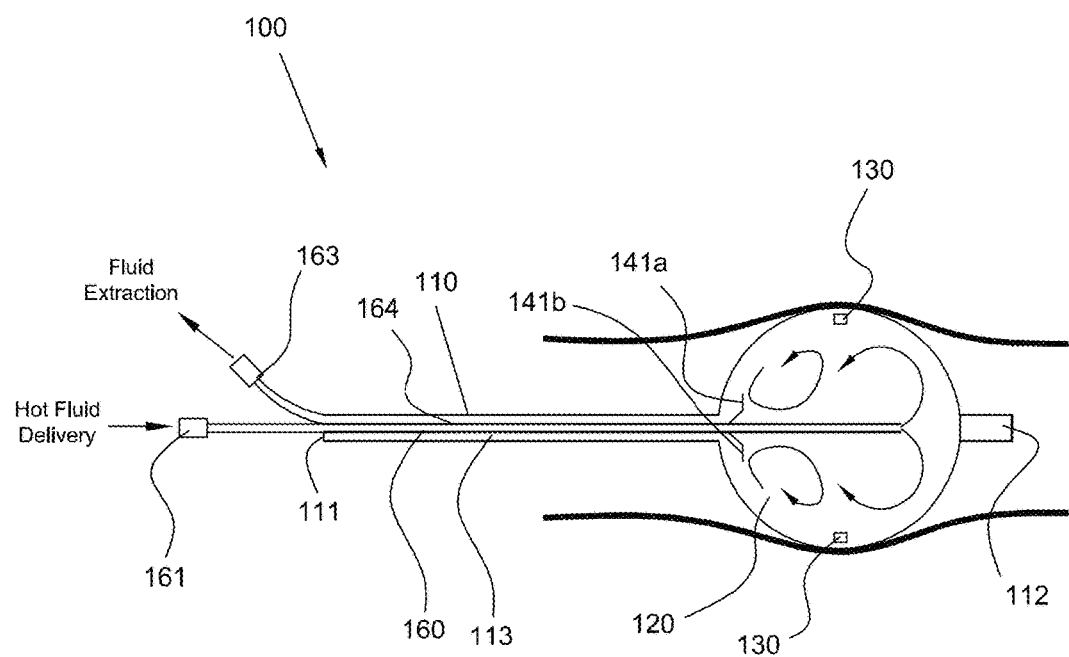
FIG. 15 is a side view of an ablation device positioned in a body lumen, the ablation device comprising flow directors for directing flow of heated fluid, consistent with the present inventive concepts.

FIG. 15 illustrates a device for treating tissue, positioned in a body lumen and including flow directors, in accordance with the present inventive concepts. Device 100 is of similar construction, and includes components similar to device 100 of FIGS. 4A and 4B. In the embodiment illustrated in FIG. 15, uniform temperature within balloon 120 and along its surface may be accomplished by means of mixing a hot fluid as it flows over at least one deflector. For example, fins 141a and 141b can be strategically placed within balloon 120 and/or lumens 160 and/or 113 leading to balloon 120 to achieve the mixing of a hot fluid entering port 161. In the embodiment shown in FIG. 15, fluid is delivered through port 161 such that it enters balloon 120 via the distal end of lumen 160. In an alternative embodiment, fluid may be delivered to balloon 120 via lumen 113, and extracted from balloon 120 via lumens 160.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 16:
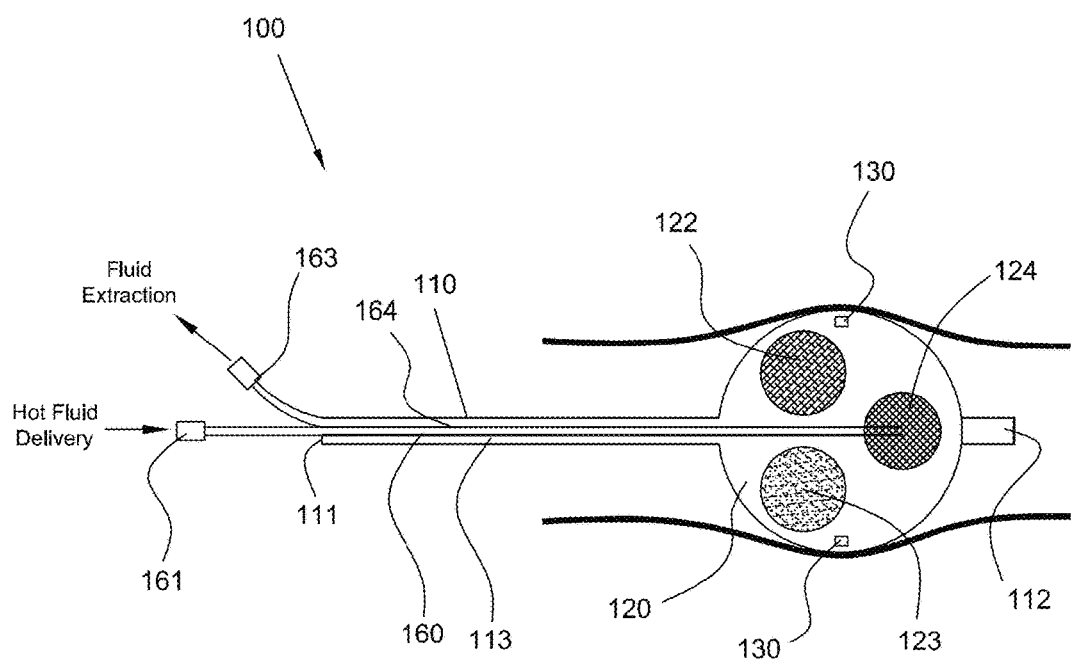
FIG. 16 is a side view of an ablation device positioned in a body lumen, the ablation device comprising an expandable balloon with one or more surface modifications, consistent with the present inventive concepts.

FIG. 16 illustrates a device for treating tissue, positioned in a body lumen and including a balloon with one or more surface modifications, in accordance with the present inventive concepts. Device 100 is of similar construction, and includes components similar to device 100 of FIGS. 4A and 4B. In the embodiment illustrated in FIG. 16, rapid and efficient heat transfer through the wall of balloon 120 may be accomplished by means of a surface modification of balloon 120. Surface modifications may include coating 122, for example, a thin-film metallization coating. Alternatively or additionally, coating 122 may comprise a coating including soft and highly compliant materials, such as hydrogels which are constructed and arranged to conform to various textures of the target tissue. Coating 122 may be configured to possess enhanced thermal conductivity. Alternatively or additionally, a surface modification may include impregnation of the wall of balloon 120 with heat transfer compounds 123, such as metallic powders. Alternatively or additionally, the surface modification may include over-sheathing balloon 120 with one or more expandable heat transfer elements, such as mesh 124, typically a wire mesh or other mesh with rapid heat transfer capabilities. These and other surface modifications may have the effect of increasing the effective thermal conductivity and heat transfer coefficient of the balloon surface in contact with the target tissue.

Alternatively or additionally, rapid and efficient heat transfer through the wall of the balloon may be accomplished by means of surface texturing to the outer surface of balloon 120, such as to increase surface area contact with non-smooth tissue. Certain target tissue, notably intestinal tissue, may possess folds, bumps and finger-like projections (villi). In one embodiment, improved engagement with non-smooth tissue may be accomplished by providing the balloon with projections, not shown, but projections sized and oriented to interdigitate with the tissue.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 17:
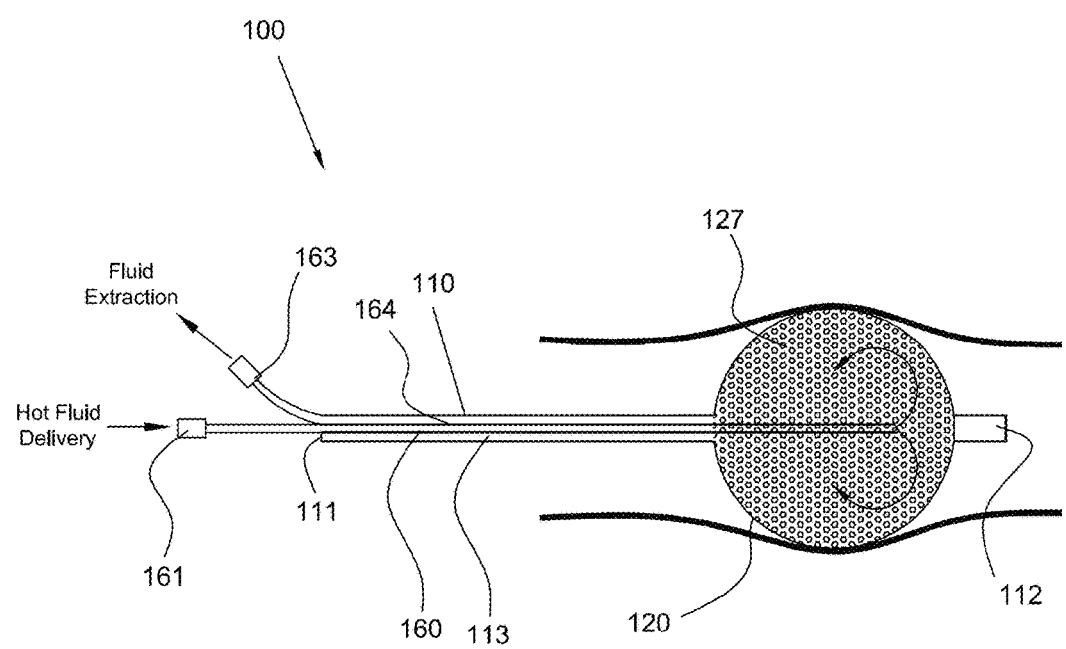
FIG. 17 is a side view of an ablation device positioned in a body lumen, the ablation device comprising an expandable balloon with a permeable portion, consistent with the present inventive concepts.

FIG. 17 illustrates a device for treating tissue, positioned in a body lumen and including a permeable balloon, in accordance with the present inventive concepts. Device 100 is of similar construction, and includes components similar to device 100 of FIGS. 4A and 4B. In the embodiment illustrated in FIG. 17, balloon 120 includes at least a portion that contains holes, pores or otherwise is permeable, permeable membrane 127. During treatment, a biocompatible hot fluid is secreted through membrane 127, contacting the target tissue, thus effecting enhanced heat transfer. The rate of seepage or "weeping" of the fluid is selected to be of such a rate as to be easily conveyed away or drained by the organ or easily suctioned and conveyed away by a conduit that is placed in communication with the lumen of the target tissue, for example lumen 160 and/or lumen 113. The placement and pattern of perforations may be chosen to suit the application geometry and the target tissue. Various means are available for the creation of permeable balloon membranes including but not limited to: laser perforation; e-beam perforation; mechanical perforation; foaming fabrication; and combinations of these. In some embodiments, balloon 120 comprises a material that becomes porous when expanded, such as a thin material that becomes porous when expanded. Balloon 120 may be fabricated using a salt or other material that is soluble in a liquid such as water, such as when balloon 120 includes salt particles that are dissolved through exposure to a liquid and create permeability in balloon 120 in the locations previously occupied by the salt particles. Balloon 120 may include a coating, such as a hydrophilic coating configured to maintain a consistently uniform, wet surface.

Device 100 typically includes at least one temperature sensor 130 constructed and arranged to measure hot fluid and/or balloon 120 temperature at any time before, during, or after the target tissue treatment. Device 100 may include numerous other types of sensors, as are described in reference to FIG. 1 hereabove. Device 100 may be part of an ablation system, such as an ablation system including a temperature controlled fluid delivery device as is described in reference to FIG. 19 herebelow.

Figure 18:
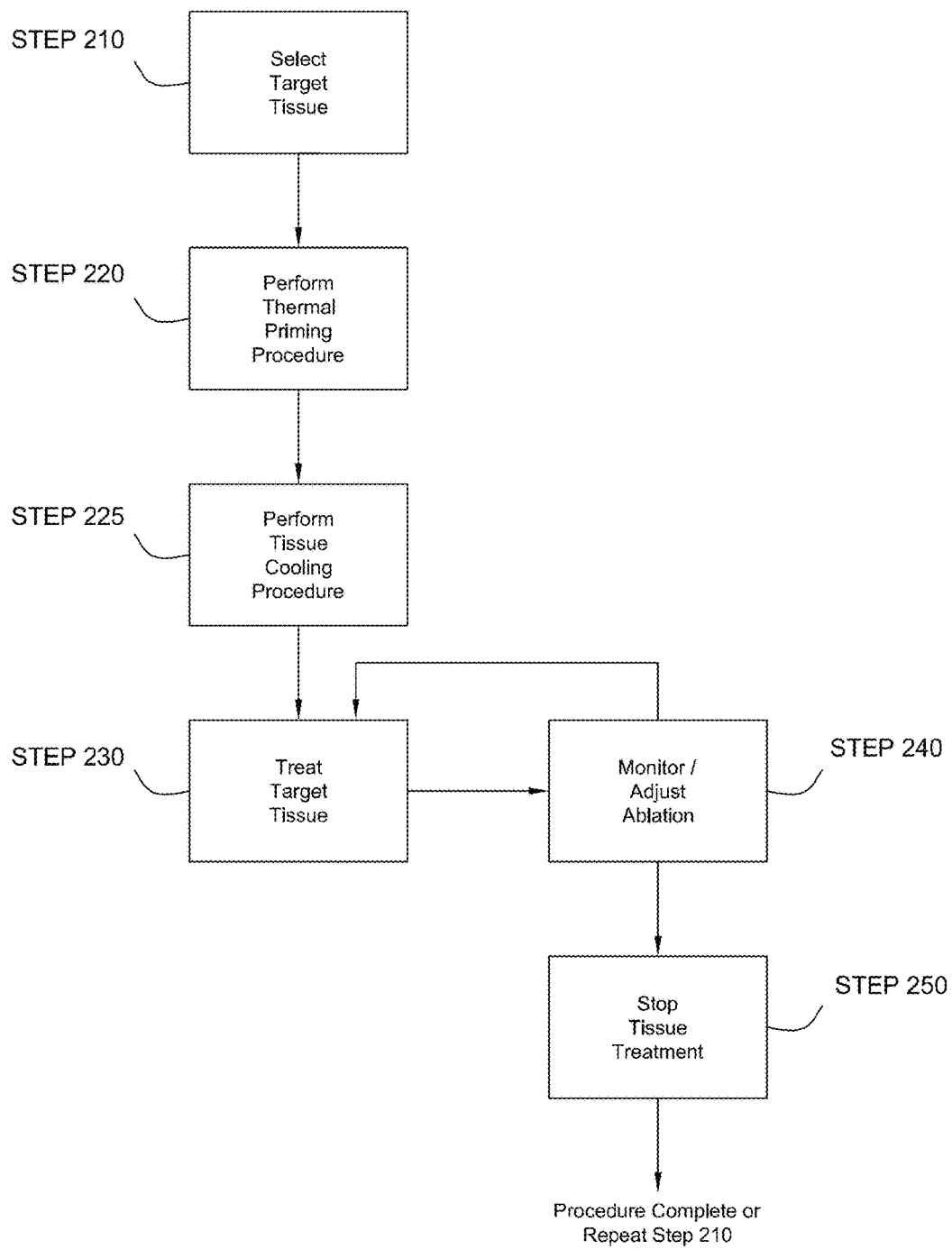
FIG. 18 is a flow chart of a method of ablating tissue, consistent with the present inventive concepts.

FIG. 18 illustrates a method of treating target tissue, in accordance with the present inventive concepts. In STEP 210, target tissue is selected, such as is described in applicant's co-pending application PCT Application Serial Number PCT/US2012/021739, entitled Devices and Methods for the Treatment of Tissue, filed Jan. 18, 2012, the contents of which are incorporated herein by reference in its entirety. In a typical embodiment, the target tissue comprises at least a length of the duodenum (e.g. approximately the entire length of the duodenum), at least a width of the duodenum (e.g. full circumferential width) and at least a depth of the duodenum (e.g. at least the mucosal layer) is selected, such as to create a target tissue volume.

The distal portion of an ablation device is delivered proximate the target tissue site, such as via a lumen of an endoscope when the target tissue comprises a portion of the gastrointestinal tract such as the duodenum. One or more treatment elements of the ablation device are positioned on or near at least a portion of target tissue, such as when the target tissue comprises multiple contiguous portions of tissue to be treated. One or more visualization devices, such as an endoscopic camera, ultrasound device, or fluoroscope may be used to position the treatment element.

In STEP 220, an optional step of thermal priming is performed, such as a delivery of fluid performed at a pressure low enough to prevent treatment element expansion or otherwise configured to avoid contact with the treatment element and target tissue. Prior to the thermal priming, a negative pressure priming procedure may be performed, such as is described in reference to FIG. 2 hereabove. Negative pressure priming can be used to remove any liquids or gases from the fluid pathways of the system, such as the fluid pathways described hereabove including lumen 160, lumen 113 and balloon 120 of FIG. 2. During thermal priming, one or more components of the ablation device may be exposed to an elevated temperature, such as fluid at an elevated temperature circulated to contact the one or more components, such as to prevent a heat-sinking effect of these components when a thermal dose of hot fluid is introduced into the treatment element to treat target tissue. During the delivery of the thermal priming fluids, a vacuum or other negative pressure may be applied to one or more outflow ports of the system.

In STEP 225, an optional step of cooling tissue is performed. This cooling may be accomplished by introducing a fluid into a treatment element, using similar or dissimilar means than are used to deliver the fluid providing the thermal dose, such as to introduce a circulating flow of cooling fluid. Alternatively, the cooling fluid may be delivered proximate or in direct contact with tissue, such as via a cooled insufflation or other cooled fluid delivered by an endoscope, the ablation device, or a separate device advanced proximate the target tissue. Typically this cooling fluid is delivered at or below 43° C., such as to cool both target and non-target tissue, such as the mucosal layer and the tunica muscularis, respectively. Safety margin tissue, such as the submucosal layer, may also be cooled. These cooling steps, typically performed at temperatures below 37° C. such as at temperatures between 4° C. and 10° C., can be used to prevent non-target tissue from being damaged in subsequent hot fluid ablation steps. In some embodiments, cooling below 4° C. may be employed, such as when one or more cooling fluids are delivered to a treatment element such as a balloon, such as a fluid with a freezing temperature below 0° C. or water maintained at a temperature just above 0° C. The duration of application of the cooling fluid can be of a fixed time period or determined by an algorithm, such as an algorithm based on a measured tissue parameter such as tissue temperature, tissue type and/or tissue thickness. In some embodiments, an algorithm is used to cool tissue until a steady-state condition is reached, such as when the surface temperature of tissue remains relatively constant, such as at a constant temperature between 4° C. and 10° C. Prior to continuing, the cooling fluid may be removed, such as by a negative pressure priming step. In addition to protecting non-target tissue, pre-cooling of target tissue may provide numerous advantages, such as improving the thermal gradient of the treatment. Cooling step 225 may be performed after target tissue treatment (e.g. after STEP 250), such as to remove residual heat from target and/or non-target tissue. In some embodiments, one or more cooling STEPs 225 are performed for a longer time duration than one or more target tissue treatment STEPs 230, such as a cooling STEP 225 that comprises a time of at least 60 seconds and a treatment STEP 230 that comprises a time less than or equal to 60 seconds. Cooling STEP 225 may include application of pressure, such as to reduce perfusion through target tissue. Cooling STEP 225 may include monitoring of temperature, such as to identify real-time temperature levels; maximum or minimum temperature levels achieved; and/or determine when a steady state temperature has been achieved.

In STEP 230, treatment of target tissue is performed. In a typical embodiment, the treatment element is inflated or otherwise expanded, such as when the treatment element is a balloon that is expanded with a hot fluid to treat the target tissue. In a different embodiment, the treatment element is already in contact with target tissue, such as from an expansion performed in STEPs 220 and/or 225, and hot fluid is introduced within the treatment element. In yet another embodiment, tubular target tissue may be brought into contact with the treatment element by application of a vacuum or other negative pressure on the walls of the tubular target tissue, such as a vacuum applied through an insufflation port of an endoscope. Sufficient apposition between the treatment element and the target tissue can be achieved and/or confirmed through pressure regulation (e.g. of hot fluid within the balloon), and/or through adequate results achieved in a leak test such as a pressurized leak test or a vacuum leak test. The leak test may comprise delivery of a fluid such as carbon dioxide proximal to the treatment element, with a sensor placed distal to the treatment element, such as the chemical sensor described in reference to FIG. 19 herebelow. Additionally or alternatively, other leak tests can be used, such as the introduction of a fluid to achieve a resultant positive pressure within a lumen of target tissue, where monitoring of the decay of the resultant positive pressure can be used to identify inappropriate apposition of the treatment element. Alternatively a vacuum or other negative pressure can be applied (e.g. as described hereabove to bring tubular target tissue in contact with a treatment element), and the decay in vacuum used to indicate adequacy of apposition of the treatment element. Required pressures and/or balloon inflation diameters may be recorded for pre-configuration used in further treatment steps. Proper apposition requirements may be determined prior to delivery of the hot ablative fluid, such as with a body temperature fluid such as air at or near body temperature.

Prior to treatment of the target tissue, a tissue layer expansion procedure may be performed, such as when the target tissue comprises mucosal tissue of the duodenum and a submucosal tissue injection is performed. In one embodiment, a submucosal injection procedure is performed as is described in applicant's co-pending application PCT Application Serial Number PCT/US2012/021739, entitled Devices and Methods for the Treatment of Tissue, filed Jan. 18, 2012, the contents of which are incorporated herein by reference in its entirety. Initiation of ablation steps may be performed soon after completion of a tissue layer expansion, such as within 15 minutes of a tissue layer expansion, typically within 10 minutes of tissue layer expansion. In some embodiments, initiation of ablation steps is performed within 5 minutes of tissue layer expansion.

Ablation of the target tissue performed in STEP 230 may be performed using the rapid rise time and rapid response systems, devices and methods described hereabove. In a typical embodiment, thermal rise-time is rapid, such as a thermal rise time in which fluid temperature within the treatment element reaches 90% of a target temperature within 5 seconds of initiating the treatment element inflation. In another typical embodiment, thermal response time is rapid, such as a thermal response time in which fluid temperature in the treatment element reaches 90% of a modified target temperature within 15 seconds of initiating the process to modify the delivery element fluid to the new target temperature.

In STEP 240, the tissue treatment is monitored, such as by monitoring signals from one or more sensors, typically one or more temperature sensors and/or one or more sensors as are described in reference to FIG. 19 herebelow. Treatment STEP 230 and monitoring STEP 240 are continued simultaneously and/or cyclically sequentially until it is determined that adequate treatment has been performed. During the cycling between STEPS 230 and 240, one or more additional steps may be performed such as steps selected from the group consisting of: negative pressure priming; tissue cooling; treatment element repositioning; treatment element apposition confirmation; target tissue radial expansion such as through insufflation; target tissue radial compression such as through the application of a negative pressure to the target tissue through an endoscope; and combinations of these. In some embodiments, rapid delivery of heating fluids followed by cooling fluids are performed to provide a thermal energy transfer with sufficient control to precisely ablate target tissue while avoiding damage to non-target tissue.

STEP 250 follows in which treatment of target tissue is stopped. In one embodiment, the expandable treatment element is deflated or otherwise compacted, such as to remove the treatment element from the target tissue site and the body, or to move the treatment element to a different portion of target tissue to be treated. In a different embodiment, the fluid in the treatment element is brought to a temperature sufficient to stop treatment, such as a temperature at or at least 10° C. below a target treatment temperature or a temperature below 43° C., such as when the treatment element had previously been filled with fluid at an elevated, ablative temperature. In order to stop target tissue treatment, the fluid in the treatment element may receive a cooling fluid, such as a fluid delivered through an inflow port while a vacuum or other negative pressure is applied to one or more outflow ports. In yet another embodiment, tubular target tissue may be moved away from the treatment element, such as through the introduction of a fluid at a positive pressure, such as the introduction of a gas such as $CO_2$ applied through an insufflation port of an endoscope. In yet another embodiment, the treatment element is translated (e.g. advanced distally or retracted proximally) from a first target tissue portion to a second target tissue portion, without deflation or otherwise losing apposition with tissue. This translation is performed such that treatment of the first target tissue portion is completed and treatment of the second target tissue portion is initiated, noting that the first target tissue portion and the second target tissue portion may include overlap.

STEPS 210 through 250 are typically repeated a number of times, such as to treat multiple contiguous subportions of target tissue, such as multiple contiguous portions of duodenal tissue. Each target tissue portion may be unique, or there may be overlap from segment to segment. A formulated approach to quantity of tissue overlap may be used, such as an overlap of approximately 5 mm to 10 mm of one or more dimensions of target tissue (e.g. length or width). Alternatively, overlap may comprise advancing and/or withdrawing the treatment element (e.g. a balloon) by a distance equal to one-half to three-quarters of its length, for each hot fluid energy delivery. Overlap amounts may vary, such as due to variances in the anatomy. In some embodiments, treatment of luminal tissue such as duodenal tissue comprises different overlap amounts in one or more angulated or otherwise non-linear portions, such as overlaps that are greater on an inside curve than an outside curve in a bend portion. Overlap amounts are typically chosen to avoid non-treated portions of target tissue. Overlapping advancements may be performed manually by an operator. Alternatively, the system and/or ablation device of the present inventive concepts may comprises an automated advancement or retraction positioning system to ensure a predetermined length of overlap from one tissue treated tissue portion to another, such as the positioning system described in reference to FIG. 19 herebelow. Alternatively or additionally, amount of overlap may be determined through visual and/or sensorial cues, such as a cue generated from: visual image provided by an endoscopic camera; impedance measurement performed by an ablation device electrode; and combinations of these. In one embodiment, a scan or other diagnostic test to confirm contiguous ablation of target tissue is performed, such as after STEP 250, after which identified untreated segments of target tissue are subsequently treated. A first portion of target tissue treatment may be followed by a second portion of target tissue treatment after a time delay, such as a delay sufficient to allow the first target tissue portion to cool. A chosen time may be selected such as to allow the first target tissue to cool to a temperature less than 43° C., such as a temperature within 2° C. of a baseline temperature such as body temperature. Alternatively or additionally, a cooling procedure may be performed between treatment of the first portion of target tissue and the second portion of target tissue.

In STEP 240, the progress of thermal ablation may be monitored by measuring and interpreting the residual heat present in the target tissue during the time interval between heat application cycles. This information may be used to fine-tune or optimize the ablative treatment of the target tissue. Residual heat is herein defined as an elevation of tissue temperature above normal body temperature at the completion of a heat application. Residual heat is expected to be a measure of the progress of thermal ablation as it represents that portion of the heat load that has not been dissipated by the target tissue. The presence of residual heat may not necessarily indicate that ablation has occurred, but may instead indicate that ablation is being approached. Target tissue that has been damaged or necrosed would be expected to exhibit increased residual heat, such as due to the complete or partial shut-down of blood perfusion. Therefore, the magnitude of residual heat is expected to be a useful indication of the progress toward and the eventual completion of ablation. The magnitude of residual heat may also be influenced by the physiological effect described hereabove, namely, increased blood perfusion due to the application of heat to soft tissue. This effect may be manifested in the early stages of ablation and therefore may be a useful indicator of the progress towards ablation.

Residual heat may be measured by means of one or more miniature temperature sensors located within the cavity of the balloon or other treatment element, or on its surface. Experiments have confirmed that residual heat passes readily into a deflated balloon, provided that the balloon remains within the treatment zone. Alternatively, the balloon may be inflated with air or any other gas or liquid between treatment cycles, for the purpose of establishing direct contact with the target tissue for the measurement of residual heat.

Prior to and/or during the treatment applied in STEP 230, a combination of treatment element (e.g. balloon) compliance and internal pressure may be used to smooth tissue folds, distend tissue, accommodate variations in tissue structure and geometry, and/or generally establish uniform circumferential contact between the balloon and the target tissue.

Prior to and/or during the treatment applied in STEP 230, the treatment element may be translated and/or spun, permitting control of thermal contact time as well as, optionally, a combination of thermal and mechanical action on the target tissue. The adjustment of thermal contact time by way of treatment element motion is to be understood as a means of adjusting thermal dose during treatment.

The treatment applied in STEP 230 may comprise treatment with a hot fluid balloon as well as other treatment means, which may also reside on the same catheter or delivery device as the hot balloon or, alternatively, be deployed on a separate device.

In some embodiments, a fluid may be introduced at the beginning of a treatment that is different than fluid delivered at a later time. Alternatively or additionally, an initial target temperature of a thermal dose may be higher than a subsequent, modified target temperature. The effect of these higher initial temperatures will cause the target tissue temperature to rise faster than if a lower initial temperature fluid or target temperature is used. Prior to the target tissue reaching a level equating to these initial fluid and/or target temperatures, a lower fluid and/or target temperature is used. This configuration increases the thermal rise of target tissue temperature, while avoiding longer term exposure of tissue to these higher temperatures, such as to reduce damage to non-target tissue.

Negative pressure priming, such as the negative pressure priming described hereabove as an optional portion of STEP 220, can be performed after one or more previous tissue treatments have been performed, such as to remove one or more fluids that would otherwise cool a fluid delivered as a thermal dose, thus improving the rise time of the thermal dose.

Tissue cooling, such as the tissue cooling performed in STEP 225, can be performed after one or more previous tissue treatments have been performed, such as to remove thermal energy from tissue. The removal of this thermal energy can be used to precisely ablate certain layers of tissue while leaving deeper layers undamaged, such as to prevent damage to non-target tissue while fully ablating target tissue. The duration of application of the cooling fluid can be of a fixed time period or determined by an algorithm, such as an algorithm based on a measured tissue parameter such as tissue temperature, tissue type and/or tissue thickness. Tissue cooling may be used when overlapping target tissue segments are treated, such as when non-target tissue proximate a tissue segment has been elevated to a temperature approaching 43° C. Tissue cooling may be delivered to bring the non-target tissue to approximately 37° C. such as during a cooling procedure including a balloon filled with fluid at approximately 37° C. Alternatively, tissue tooling may be delivered to bring the non-target tissue to a level lower than 37° C., such as during a cooling procedure including a balloon filled with fluid between 4° C. and 10° C.

Referring now to FIG. 19, a system for ablating or otherwise treating target tissue is illustrated, consistent with the present inventive concepts. System 300 is constructed and arranged to treat target tissue 10, including one or more tissue portions. System 300 may include one or more ablation devices, such as those described hereabove. In the embodiment of FIG. 19, system 300 includes a multiple filament elongate device 301 comprising shafts 311a and 311b. In some embodiments, device 301 comprises a flexible portion with a diameter less than 6 mm and a length of 100 cm or longer. Shaft 311a has a distal end 312. Shafts 311a and 311b are sized and configured such that shaft 311a is slidingly received by shaft 311b. Shafts 311a and 311b have been inserted through a working channel (e.g. a 6 mm working channel), lumen 351, of endoscope 350. Shafts 311a and 311b may be inserted over a guidewire, such as guidewire 371 shown exiting distal end 312. Device 301 further includes two expandable tissue treatment elements, expandable treatment element 322a, and expandable treatment element 322b, mounted to shafts 311a and 311b, respectively. Treatment elements 322a and 322b may be configured in various forms to treat the target tissue, such as in one or more of the treatment element forms described in applicant's co-pending application PCT Application Serial Number PCT/US2012/021739, entitled Devices and Methods for the Treatment of Tissue, filed Jan. 18, 2012, the contents of which are incorporated herein by reference in its entirety. In one embodiment, elements 322a and 322b comprise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In another embodiment, treatment element 322a comprises an abrasive element configured for abrading tissue; and treatment element 322b comprises an energy delivery element such as an energy delivery element configured to deliver RF energy. Shafts 311a and 311b may include one or more lumens passing therethrough, and may comprise wires or optical fibers for transfer of data and/or energy. Expandable treatment element 322b typically comprises a treatment element constructed and arranged such as balloons 120 referred to in FIGS. 1 through 17 hereabove. Shaft 311b may comprise one or more shafts, such as one or more concentric shafts configured to delivery and/or recirculated hot fluid through treatment delivery element 322b, such as to deliver a bolus of hot fluid energy or other thermal dose of the present inventive concepts. Device 301 may comprise a single treatment element 322b without inclusion of treatment element 322a and its associated components, similar to devices 100 described in reference to FIGS. 1 through 17 hereabove.

Endoscope 350 may be a standard endoscope, such as a standard gastrointestinal endoscope, or a customized endoscope, such as an endoscope including sensor 353 configured to provide information related to the tissue treatment of the present inventive concepts. Sensor 353 and the other sensors of system 300 may be a sensor selected from the group consisting of: heat sensors such as thermocouples; impedance sensors such as tissue impedance sensors; pressure sensors; blood sensors; optical sensors such as light sensors; sound sensors such as ultrasound sensors; electromagnetic sensors such as electromagnetic field sensors; and combinations of these. Sensor 353 may be configured to provide information to one or more components of system 300, such as to monitor the treatment of target tissue 10 and/or to treat target tissue 10 in a closed loop fashion. Energy delivery may be modified by one or more sensor readings. In one embodiment, an algorithm processes one or more sensor signals to modify amount of energy delivered, power of energy delivered and/or temperature of energy delivery.

A sensor such as a chemical detection sensor may be included, such as to confirm proper apposition of treatment elements 322a and/or 322b. In this configuration, a chemical sensor such as a carbon dioxide sensor can be placed distal to treatment element 322a and/or 322b, and a fluid such as carbon dioxide gas is introduced proximal to the treatment element 322a and/or 322b. Detection of the introduced fluid may indicate inadequate apposition of treatment element 322a and/or 322b, such as to prevent inadequate transfer of energy to the target tissue.

Endoscope 350 may include camera 352, such as a visible light, ultrasound and/or other visualization device used by the operator of system 300 prior to, during or after the treatment of target tissue 10, such as during insertion or removal of endoscope 350 and/or shafts 311a and 311b. Camera 352 may provide direct visualization of internal body spaces and tissue, such as the internal organs of the gastrointestinal tract. Endoscope 350 may be coupled with or otherwise include a guidewire, such as to allow insertion of endoscope 350 into the jejunum.

System 300 may be configured to perform insufflation of the body lumen. The body lumen may be pressurized, such as by using one or more standard insufflation techniques and/or a technique as described in reference to FIGS. 8A and 8B hereabove, for example. Insufflation fluid may be introduced through lumen 354 of endoscope 350. Lumen 354 travels proximally and connects to a source of insufflation liquid or gas, not shown, but typically a source of air, $CO_2$ and/or water. Alternatively or additionally, insufflation fluid may be delivered by device 301, such as through shaft 311a and/or 311b, or through a port in treatment element 322a and/or 322b, ports not shown but fluidly attached to a source of insufflation liquid or gas, also not shown. Alternatively or additionally, a separate device, configured to be inserted through endoscope 350 or to be positioned alongside endoscope 350, may have one or more lumens configured to deliver the insufflation fluid. System 300 may include one or more occlusive elements or devices, such as expandable treatment element 322a or another expandable device, not shown but configured to radially expand such as to fully or partially occlude the body lumen, such that insufflation pressure can be achieved and/or maintained over time (e.g. reduce or prevent undesired migration of insufflation fluid). The one or more occlusive elements or devices may be positioned proximal to and/or distal to the luminal segment to be insufflated.

The treatment elements of the present inventive concepts, such as treatment elements 322a and/or 322b of FIG. 19, may have a fixed diameter or they may be expandable. Expandable elements may comprise inflatable balloons, expandable cages, radially deployable arms, and the like. Treatment elements may include an energy delivery element or arrays of elements, such as an array of balloon lobes for delivery of thermal energy from a hot fluid. Energy delivery elements may be configured to deliver one or more different forms of energy. Energy may be delivered in constant or varied magnitudes or other energy levels. Energy may be continuous or pulsed, and may be delivered in a closed-loop fashion. Energy delivery may be varied from a first tissue location to a second location, such as a decrease in energy from a first treated location to a second treated location when the second treated location is thinner than the first treated location. Alternatively or additionally, energy delivery may be varied during a single application to a single tissue location, such as by adjusting the amount of energy delivered, or by moving a portion of the energy delivery element, such as by deflating an energy delivery element as has been described in detail hereabove.

Treatment elements 322a and/or 322b may be configured to cause the complete or partial destruction of the target tissue, such as the complete or partial destruction of the duodenal mucosa. Treatment elements 322a and/or 322b may be configured to remove previously treated and/or untreated tissue. Pressure maintained within treatment elements 322a and/or 322b can be set and/or varied to adjust the treatment being performed such as to: adjust the depth of treatment; adjust the force applied by a mechanical abrasion device; adjust the amount of energy applied during thermal energy delivery (e.g. by changing tissue contact); and combinations of these.

Treatment elements 322a and 322b may include sensors 316a and 316b, respectively. Sensors 316a and 316b may each be one or more sensors as described hereabove. Sensor 316a may be a sensor configured to provide information related to the tissue treatment performed by treatment element 322a, such as a visualization sensor mounted to treatment element 322a that is configured to differentiate tissue types that are proximate treatment element 322a, such as to differentiate mucosal and submucosal tissue. Sensor 316b may be a sensor configured to provide information related to the tissue treatment performed by treatment element 322b, such as a temperature sensor mounted to treatment element 322b and configured to monitor the temperature of treatment element 322b and/or tissue proximate treatment element 322b.

Energy Delivery and Fluid Transport Unit (EDU) 330 may be configured to deliver and extract one or more fluids from treatment element 322a and/or 322b, as well as deliver one or more forms of energy to target tissue. In one embodiment, EDU 330 is configured to deliver one or more supplies of hot fluid, such as hot water or saline to a balloon treatment element. In these embodiments, EDU 330 typically includes one or more fluid pumps, such as one or more peristaltic, displacement or other fluid pumps; as well as one or more heat exchangers or other fluid heating elements internal or external to device 301. EDU 330 may be constructed and arranged to rapidly deliver and/or withdraw fluid to and/or from treatment elements 322a and/or 322b with one or more fluid transport means. Fluid transport means may include a pump configured to deliver fluid at a flow rate of at least 50 ml/min and/or a pump or vacuum source configured to remove fluid at a flow rate of at least 50 ml/min. A pump or vacuum source may be configured to continuously exchange hot fluid and/or to perform a negative pressure priming event to remove fluid from one or more fluid pathways of device 301. EDU 330 and/or device 301 may include one or more valves in the fluid delivery and/or fluid withdrawal pathways, such as the valves described in reference to FIG. 11A-B hereabove or one or more other valves in the fluid pathway with treatment element 322a and/or 322b. Valves may be configured to control entry of fluid into an area and/or to maintain pressure of fluid within an area. Valves may be used to transition from a heating fluid, such as a fluid of 90° C. maintained in a treatment element for approximately 12 seconds, to a cooling fluid, such as a fluid between 4° C. and 10° C. maintained in the treatment element for approximately 30 to 60 seconds. Typical valves include but are not limited to: duck-bill valves; slit valves; electronically activated valves; pressure relief valves; and combinations of these. EDU 330 may be configured to rapidly inflate and/or deflate treatment elements 322a and/or 322b, such as has been described hereabove. EDU 330 may be configured to purge the fluid pathways of device 301 with a gas such as air, such as to remove cold or hold fluid from device 301 and/or to remove gas bubbles from device 301.

In another embodiment, EDU 330 is configured to deliver at least radiofrequency (RF) energy, and system 300 includes ground pad 332 configured to be attached to the patient (e.g. on the back of the patient), such that RF energy can be delivered in monopolar delivery mode. Alternatively or additionally, EDU 330 may be configured to deliver energy in a bipolar RF mode, such as when treatment element 322b is configured to deliver RF energy and/or system 300 includes a second energy delivery element, not shown but typically including one or more electrodes or electrically conductive surfaces.

System 300 may include controller 360, which typically includes a graphical user interface, not shown but configured to allow one or more operators of system 300 to perform one or more functions such as entering of one or more system input parameters and visualizing and/or recording of one or more system output parameters. Typical system input parameters include but are not limited to: temperature of a fluid to be delivered to a treatment element such as a balloon; temperature of a cooling fluid to be delivered; flow rate of a hot fluid to be delivered; volume of a hot fluid to be delivered; type of energy to be delivered such as RF energy, thermal energy and/or mechanical energy; quantity of energy to be delivered such as a cumulative number of joules of energy to be delivered or peak amount of energy to be delivered; types and levels of combinations of energies to be delivered; energy delivery duration; pulse width modulation percentage of energy delivered; number of reciprocating motions for an abrasive device to transverse; temperature for a treatment element such as target temperature or maximum temperature; insufflation pressure; insufflation duration; and combinations of these. System input parameters may include information based on patient anatomy or conditions such as pre-procedural or peri-procedural parameters selected from the group consisting of: mucosal density and/or thickness; mucosal "lift" off of submucosa after a submucosal injection; longitudinal location of target tissue within the GI tract; and combinations of these. Typical system output parameters include but are not limited to: temperature information such as tissue and/or treatment element temperature information; pressure information such as balloon pressure information or insufflation pressure information; force information such as level of force applied to tissue information; patient information such as patient physiologic information recorded by one or more sensors; and combinations of these.

Controller 360 and/or one or more other components of system 300 may include an electronics module, such as an electronics module including a processor, memory, software, and the like. Controller 360 is typically configured to allow an operator to initiate, modify and cease treatment of tissue by the various components of system 300, such as by controlling EDU 330. Controller 360 may be configured to adjust the temperature, flow rate and/or pressure of fluid delivered to expandable treatment element 322a and/or 322b. Controller 360 may be configured to initiate insufflation and/or to adjust insufflation pressure. Controller 360 may be configured to deliver energy (e.g. from EDU 330) or other tissue treatment in a closed-loop fashion, such as by modifying one or more tissue treatment parameters based on signals from one or more sensors of system 300. Controller 360 may be programmable such as to allow an operator to store predetermined system settings for future use. System 300, EDU 330 and/or controller 360 may be constructed and arranged to modify the temperature, flow rate and/or pressure of a fluid delivered to one or more treatment elements based a parameter selected from the group consisting of: one or more measured properties of the delivered fluid; one or more measured properties of the treatment element; one or more measured properties of the target tissue; and combinations of these.

Controller 360 and EDU 330 may be configured to deliver energy in constant, varied, continuous and discontinuous energy delivery profiles. Pulse width modulation and/or time division multiplexing (TDM) may be incorporated to achieve precision of energy delivery, such as to ensure ablation of target tissue while leaving non-target tissue intact.

System 300 may include a mechanism configured to apply motion to treatment elements 322a and/or 322b, such as motion transfer element 335. Motion transfer element 335 may be configured to rotate and/or axially translate shafts 311a and/or 311b such that treatment elements 322a and/or 322b, respectively, are rotated and/or translated. Motion transfer element 335 may be configured to rotate treatment elements 322a and 322b independently or in unison. Motion transfer element 335 may include one or more rotational or linear drive assemblies, such as those including rotational motors, magnetic and other linear actuators, and the like which are operably connected to shaft 311a and/or 311b. Shafts 311a and/or 311b are constructed with sufficient column strength and/or torque transfer properties to sufficiently rotate and/or translate treatment elements 322a and/or 322b, respectively, during associated tissue treatment. Motion transfer element 335 may be in communication with controller 360, such as to activate, adjust and/or otherwise control motion transfer element 335 and thus the motion of treatment element 322a and/or treatment element 322b. Motion transfer element 335 may be manually driven and/or automatically (e.g. motor) driven. Alternatively or additionally, motion transfer element 335 may be used to advance or retract treatment element 322a and/or 322b from a first position to treat a first portion of target tissue, to a second position to treat a second portion of target tissue. In this embodiment, repositioning of treatment element 322a and/or 322b may be configured to provide overlapping treatment, such as the overlapping treatment described in reference to FIG. 18 hereabove.

Controller 360 may be configured to control energy delivery, such as controlling energy delivery to treatment element 322a and/or 322b. For example, if treatment element 322b is an RF electrode array, and energy delivery unit 330 comprises an RF generator, controller 360 may be programmed to provide a specific amount of RF energy for a defined period of time. In another example, if treatment element 322b is a heated saline balloon, then controller 360 can be configured to provide and withdraw heated saline to treatment element 322b, such as through an energy transfer tube not shown, at a desired temperature and for a desired time period. Controller 360 may be configured for manual control, so that the operator first initiates the energy delivery, then allows the treatment element 322b to ablate the tissue for some time period, after which the operator terminates the energy delivery.

System 300 may further include one or more imaging devices, such as imaging device 370. Imaging device 370 may be configured to be inserted into the patient and may comprise a visual light camera; an ultrasound imager; an optical coherence domain reflectometry (OCDR) imager; and/or an optical coherence tomography (OCT) imager, such as when integral to, attached to, contained within and/or proximate to shaft 311a and/or 311b. Imaging device 370 may be inserted through a separate working channel of endoscope 350, lumen not shown. In one embodiment, imaging device 370 is an ultrasound transducer connected to a shaft, not shown but surrounded by shaft 311a and typically rotated and/or translated to create a multi-dimensional image of the area surrounding imaging device 370. Alternatively or additionally, imaging device 370 may be external to the patient, such as an imaging device selected from the group consisting of: an X-ray; a fluoroscope; an ultrasound image; an MRI; a PET Scanner; and combinations of these.

System 300 may further include protective cap 380, configured to be positioned proximate tissue to prevent damage to certain tissue during energy delivery or other tissue treatment event. Protective cap 380 may be delivered with endoscope 350 or another elongate device such that cap 380 can be placed over and then positioned to protect the Ampulla of Vater. In a typical embodiment, protective cap 380 is removed within 24 hours of placement, such as by being removed during the procedure after treatment of the target tissue.

System 300 may further include a tissue expanding device 390, configured to expand the target tissue area, such as sub-mucosal tissue expanding device. Tissue expansion can greatly alleviate the need for precision of treatment, such as precision of energy delivery, due to the increased size (e.g. increased depth) of the target and an associated safety zone of tissue to which treatment causes no significant adverse event (e.g. an expanded submucosal layer prior to a mucosal layer ablation).

System 300 may further include one or more pharmaceutical or other agents 500, such as an agent configured for systemic and/or local delivery to a patient. These agents may be delivered, pre-procedurally, peri-procedurally and/or post-procedurally. The agents may be configured to improve healing, such as agents selected from the group consisting of: antibiotics, steroids, mucosal cytoprotective agents such as sucralfate, proton pump inhibitors or other acid blocking drugs; and combinations of these. Alternative or in addition to these agents, pre-procedural and/or post-procedural diets may be employed. Pre-procedural diets may include food intake that is low in carbohydrates and/or low in calories. Post-procedural diets may include food intake that comprise a total liquid diet or a diet that is low in calories and/or low in carbohydrates.

In a typical embodiment, system 300 does not include a chronically implanted component or device, only body inserted devices that are removed at the end of the clinical procedure or shortly thereafter, such as devices removed within 8 hours of insertion, within 24 hours of insertion and/or within one week of insertion. In an alternative embodiment, implant 510 may be included. Implant 510 may comprise one or more of: a stent; a sleeve; and a drug delivery device such as a coated stent, a coated sleeve and/or an implanted pump.

Each of the components of system 300 may be removably attached to another component, particularly controller 360, EDU 330, motion transfer element 335, ground pad 332 and endoscope 350 and elongate device 301.

Numerous embodiments of the systems, methods and devices for treating target tissue described hereabove include the delivery of a hot fluid, such as fluid delivered at a temperature above 43° C., typically above 60° C., to deliver a thermal dose to at least a portion of the target tissue. One or more cooling fluids may be delivered to limit the thermal dose and/or to rapidly decrease the delivery of heat energy to tissue. In some alternative embodiments, a chilled fluid, such as a fluid below 20° C., typically below 0° C. is used to deliver a thermal dose to ablate tissue, such as through the incorporation of a cryogenic source configured to chill fluid delivered to an expandable treatment element such as one or more balloons. In these cryogenic ablation embodiments, a warming fluid may be delivered to limit the thermal dose and/or to rapidly decrease an ongoing cryogenic ablation.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system for treating target tissue, the system comprising:
    an ablation device comprising:
        an elongate tube with a proximal portion, a distal portion, and at least one lumen extending from the proximal portion to the distal portion; and
        an expandable treatment element mounted to the elongate tube distal portion and in fluid communication with the at least one lumen;
        an energy delivery unit constructed and arranged to deliver a cooling fluid from the energy delivery unit through the at least one lumen in the elongate tube to the expandable treatment element to cool the target tissue and to deliver a heated fluid from the energy delivery unit through the at least one lumen in the elongate tube to the expandable treatment element to ablate the target tissue, wherein the energy delivery unit is configured to deliver the heated fluid at a temperature sufficient to ablate the target tissue; and
    a controller configured to cause the energy delivery unit to deliver the cooling fluid to the target tissue to cool the target tissue to a steady state temperature prior to delivery of the heated fluid at the temperature sufficient to ablate the target tissue and thereafter to cause the energy delivery unit to again deliver the cooling fluid to the target tissue after ablating the target tissue.

2. The system according to claim 1, wherein the target tissue is a tissue lining of an interior of a hollow body organ and the controller is configured to modulate the temperature of the heated fluid to deliver a thermal dose to ablate the tissue lining of the interior of the hollow body organ while avoiding other damage to the hollow body organ.

3. The system according to claim 2, wherein the controller is configured to modulate the thermal dose to ablate duodenal mucosa while avoiding damage to duodenal serosa.

4. The system according to claim 2, wherein the controller is configured to modulate the thermal dose to ablate the target tissue while avoiding damage to non-target tissue.

5. The system according to claim 2, wherein the system is constructed and arranged to measure an ablation parameter and adjust the thermal dose based on the measured ablation parameter.

6. The system according to claim 5, wherein the ablation parameter comprises the temperature of the heated fluid delivered to the expandable treatment element.

7. The system according to claim 2, wherein the controller is constructed and arranged to modify delivery of the thermal dose.

8. The system according to claim 7, wherein the controller is constructed and arranged to modify the temperature of at least one of the heated fluid and the cooling fluid delivered to the expandable treatment element.

9. The system according to claim 7, wherein the controller is constructed and arranged to modify at least one of the temperature, flow rate or pressure of at least one of the heated fluid and the cooling fluid delivered to the expandable treatment element based on a parameter selected from the group consisting of one or more measured properties of the at least one of the heated fluid and the cooling fluid; one or more measured properties of the expandable treatment element; and one or more measured properties of the target tissue.

10. The system according to claim 1, wherein the system is constructed and arranged to avoid damage to ampulla of Vater.

11. The system according to claim 1, wherein the cooling fluid comprises a fluid at a temperature between 4° C. and 10° C.

12. The system according to claim 1, wherein the temperature sufficient to ablate the target tissue is in a range between 65° C. and 99° C.

13. The system according to claim 12, wherein the cooling fluid comprises a temperature less than or equal to 10° C.

14. The system according to claim 1, wherein the energy delivery unit comprises at least one fluid pump constructed and arranged to deliver both the cooling fluid and the heated fluid.

15. The system according to claim 14, wherein the at least one fluid pump is constructed and arranged to deliver fluid at a flow rate of at least 50 ml/min.

16. The system according to claim 1, wherein the energy delivery unit comprises a first source of fluid comprising the cooling fluid and a second source of fluid comprising the heated fluid.

17. The system according to claim 1, wherein the energy delivery unit comprises a syringe.

18. The system according to claim 1, further comprising an inflow port and an outflow port, the inflow port and the outflow port in fluid communication with the expandable treatment element.

19. The system according to claim 18, wherein the system is further constructed and arranged to maintain the inflow port at a first pressure that is above atmospheric pressure and to maintain the outflow port at a second pressure that is lower than atmospheric pressure.

20. The system according to claim 1 wherein the expandable treatment element comprises a balloon.

21. The system according to claim 1, wherein the expandable treatment element comprises multiple balloons.

22. The system according to claim 1, wherein the expandable treatment element comprises a balloon comprising multiple chambers.

23. The system according to claim 1, further comprising a temperature sensor selected from the group consisting of a thermocouple; a thermistor; a resistance temperature detector; and an optical pyrometer.

24. The system according to claim 1, further comprising a sensor constructed and arranged to measure a parameter selected from the group consisting of pressure; fluid pressure; flow rate; temperature; fluid temperature; viscosity; density; and optical clarity.

25. The system according to claim 1, further comprising a fluid mixing assembly constructed and arranged to cause fluid mixing within the expandable treatment element.

26. The system according to claim 25, wherein the fluid mixing assembly comprises a fluid delivery tube comprising a distal delivery port and a fluid extraction tube comprising a distal extraction port, wherein the delivery port and the extraction port are positioned to cause the fluid mixing within the expandable treatment element.

27. The system according to claim 1, wherein the ablation device comprises a vacuum element constructed and arranged to move the target tissue toward the expandable treatment element to initiate delivery of energy to the target tissue.

28. The system according to claim 1, wherein the cooling fluid comprises a fluid having a temperature below 37° C.

* * * * *